United States Patent
Taziaux et al.

(10) Patent No.: US 11,484,539 B2
(45) Date of Patent: *Nov. 1, 2022

(54) COMPOUNDS AND THEIR USES FOR ALLEVIATING MENOPAUSE-ASSOCIATED SYMPTOMS

(71) Applicant: Estetra SPRL, Liege (BE)

(72) Inventors: Melanie Taziaux, Liege (BE); Glwadys Rausin, Trooz (BE); Maud Jost, Liege (BE); Marie Mawet, Angleur (BE)

(73) Assignee: Estetra SPRL, Liege (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/048,540

(22) PCT Filed: Apr. 19, 2019

(86) PCT No.: PCT/EP2019/060221
§ 371 (c)(1),
(2) Date: Oct. 16, 2020

(87) PCT Pub. No.: WO2019/202142
PCT Pub. Date: Oct. 24, 2019

(65) Prior Publication Data
US 2021/0154212 A1    May 27, 2021

(30) Foreign Application Priority Data

Apr. 19, 2018 (EP) .................... 18168234
May 30, 2018 (EP) .................... 18174985
Jan. 4, 2019 (EP) .................... 19150421

(51) Int. Cl.
*A61K 31/565* (2006.01)
*A61K 31/585* (2006.01)
*A61P 15/12* (2006.01)
*A61K 9/00* (2006.01)
*A61K 31/55* (2006.01)
*A61K 31/57* (2006.01)
*A61K 31/573* (2006.01)

(52) U.S. Cl.
CPC .......... *A61K 31/585* (2013.01); *A61K 9/0053* (2013.01); *A61K 31/55* (2013.01); *A61K 31/565* (2013.01); *A61K 31/57* (2013.01); *A61K 31/573* (2013.01); *A61P 15/12* (2018.01)

(58) Field of Classification Search
CPC .... A61K 31/585; A61K 9/0053; A61K 31/55; A61K 31/565; A61K 31/57; A61K 31/573; A61P 15/12
See application file for complete search history.

(56) References Cited

U.S. PATENT DOCUMENTS

| | | | |
|---|---|---|---|
| 3,138,588 A | 6/1964 | Smith | |
| 3,433,785 A | 3/1969 | Phillips et al. | |
| 5,164,405 A | 11/1992 | McFarlane et al. | |
| 5,340,586 A | 8/1994 | Pike et al. | |
| 6,117,446 A | 9/2000 | Place | |
| 6,723,348 B2 | 4/2004 | Faham et al. | |
| 6,992,218 B2 | 1/2006 | Dietlin et al. | |
| 7,723,320 B2 | 5/2010 | Bunschoten et al. | |
| 7,732,430 B2 | 6/2010 | Bunschoten et al. | |
| 7,871,995 B2 | 1/2011 | Bunschoten et al. | |
| 7,923,440 B2 | 4/2011 | Bunschoten et al. | |
| 7,943,604 B2 | 5/2011 | Coelingh Bennink et al. | |
| 8,026,228 B2 | 9/2011 | Coelingh Bennink et al. | |
| 8,048,869 B2 | 11/2011 | Bunschoten et al. | |
| 8,236,785 B2 | 8/2012 | Coelingh Bennink | |
| 8,367,647 B2 | 2/2013 | Coelingh Bennink et al. | |
| 8,518,923 B2 | 8/2013 | Visser et al. | |
| 8,987,240 B2 | 3/2015 | Coelingh Bennink et al. | |
| 8,987,484 B2 | 3/2015 | Pascal | |
| 9,034,854 B2 | 5/2015 | Coelingh Bennink et al. | |
| 9,040,509 B2 | 5/2015 | Coelingh Bennink et al. | |
| 9,238,035 B2 | 1/2016 | Foidart et al. | |
| 9,561,238 B2 | 2/2017 | Coelingh Bennink et al. | |
| 9,579,329 B2 | 2/2017 | Wouters et al. | |
| 9,603,860 B2 | 3/2017 | Perrin et al. | |
| 9,884,064 B2 | 2/2018 | Platteeuw et al. | |
| 9,987,287 B2 | 6/2018 | Platteeuw et al. | |
| 9,988,417 B2 | 6/2018 | Ferreirogil et al. | |

(Continued)

FOREIGN PATENT DOCUMENTS

| CL | 200501207 | 5/2005 |
|---|---|---|
| CL | 201400802 | 4/2014 |

(Continued)

OTHER PUBLICATIONS

Stanczyk et al., Endocrine Reviews, 2013;34(2):171-208 (Year: 2013).*
Bennink, et al., "Clinical of the fetal estrogen estetrol in a multiple-rising-dose study in postmenopausal women", Maturitas (2016) 91:93-100.
International Search Report and Written Opinion dated Jul. 11, 2019 for PCT Application No. PCT/EP2019/060221, filed Apr. 19, 2019.
Anderson et al., "Effects of conjugated equine estrogen in post-menopausal women with hysterectomy: the Women's Health Initiative randomized controlled trial" JAMA (2004) 291(14):1701-1712.
Archer et al., "A randomized, double-blind, placebo-controlled study of the lowest effective dose of drospirenone with 17A-estradiol for moderate to severe vasomotor symptoms in postmenopausal women" Menopause (2014) 21(3):227-235.
Bjarnason et al., "Acute and long-term estradiol kinetics in smoking postmenopausal women" Climacteric (2012)15(5):449-454.

(Continued)

*Primary Examiner* — San Ming R Hui
(74) *Attorney, Agent, or Firm* — Foley & Lardner LLP

(57) ABSTRACT

The present invention relates to a hormone replacement therapy, to the associated compounds and to the associated packaging units, for alleviating menopause-associated symptoms which is based on the administration to a female mammal of an estetrol component at a specific daily dose, optionally in combination with a progestogenic component. The therapy enjoys a statistically significant efficacy combined with a favourable profile for side effects compared to currently available methods for alleviating menopause-associated symptoms.

11 Claims, No Drawings

(56) References Cited

U.S. PATENT DOCUMENTS

| | | |
|---|---|---|
| 10,000,524 B2 | 6/2018 | Verhaar et al. |
| 10,179,140 B2 | 1/2019 | Perrin et al. |
| 10,201,611 B2 | 2/2019 | Bennink et al. |
| 10,660,903 B2 | 5/2020 | Jaspart et al. |
| 10,888,518 B2 | 1/2021 | Jaspart et al. |
| 10,894,014 B2 | 1/2021 | Jaspart et al. |
| 11,147,771 B2 | 10/2021 | Jaspart et al. |
| 2002/0132801 A1 | 9/2002 | Heil et al. |
| 2002/0193356 A1 | 12/2002 | Van Beek et al. |
| 2004/0009960 A1 | 1/2004 | Heil et al. |
| 2004/0192620 A1 | 9/2004 | Bunschoten et al. |
| 2004/0198671 A1 | 10/2004 | Bunschoten et al. |
| 2005/0032755 A1 | 2/2005 | Van Look et al. |
| 2005/0106240 A1 | 5/2005 | Tanaka et al. |
| 2005/0113350 A1 | 5/2005 | Duesterberg et al. |
| 2005/0147670 A1 | 7/2005 | Hsu et al. |
| 2006/0211669 A1 | 9/2006 | Verhaar et al. |
| 2006/0276414 A1 | 12/2006 | Coelingh Bennink et al. |
| 2007/0048369 A1 | 3/2007 | Foreman et al. |
| 2007/0286819 A1 | 12/2007 | Devries et al. |
| 2007/0286829 A1 | 12/2007 | Batista |
| 2008/0113953 A1 | 5/2008 | De Vries et al. |
| 2008/0166406 A1 | 7/2008 | Kristjansson |
| 2010/0035987 A1 | 2/2010 | Mang et al. |
| 2010/0093679 A1 | 4/2010 | Heil et al. |
| 2011/0021504 A1 * | 1/2011 | Andreella ............... A61P 19/00 540/602 |
| 2011/0250272 A1 | 10/2011 | Besse et al. |
| 2011/0250274 A1 | 10/2011 | Shaked et al. |
| 2012/0077888 A1 | 3/2012 | Ramtoola et al. |
| 2012/0128733 A1 | 5/2012 | Perrin et al. |
| 2012/0220556 A1 | 8/2012 | Heil et al. |
| 2013/0079400 A1 | 3/2013 | Riedl et al. |
| 2014/0083639 A1 | 3/2014 | Bonini et al. |
| 2014/0107091 A1 | 4/2014 | Pascal |
| 2014/0107358 A1 | 4/2014 | Pascal |
| 2014/0235882 A1 | 8/2014 | Platteeuw et al. |
| 2015/0045300 A1 | 2/2015 | Ahuja et al. |
| 2015/0182540 A1 | 7/2015 | Heil et al. |
| 2016/0101116 A1 | 4/2016 | Foidart et al. |
| 2016/0310506 A1 | 10/2016 | Platteeuw et al. |
| 2016/0367567 A1 | 12/2016 | Jaspart et al. |
| 2017/0196886 A1 | 7/2017 | Wouters et al. |
| 2017/0216318 A1 | 8/2017 | Perrin et al. |
| 2017/0369521 A1 | 12/2017 | Platteeuw et al. |
| 2018/0265540 A1 | 9/2018 | Verhaar et al. |
| 2019/0167700 A1 | 6/2019 | Jost et al. |
| 2020/0004672 A1 | 1/2020 | Scott et al. |
| 2020/0046729 A1 | 2/2020 | Jost et al. |
| 2020/0352959 A1 | 11/2020 | Jaspart et al. |
| 2021/0154211 A1 | 5/2021 | Taziaux et al. |
| 2022/0096385 A1 | 3/2022 | Jaspart et al. |

FOREIGN PATENT DOCUMENTS

| | | |
|---|---|---|
| CL | 2013003435 A1 | 8/2014 |
| CN | 1197387 A | 10/1998 |
| CN | 1780634 A | 5/2006 |
| CN | 101443015 A | 5/2009 |
| CN | 101541326 A | 9/2009 |
| CN | 101631536 A | 1/2010 |
| CN | 101780073 A | 7/2010 |
| CN | 104379148 | 2/2015 |
| CN | 102058604 A | 5/2018 |
| DE | 20 2009 018 024 U1 | 12/2010 |
| EP | 0 136 011 A2 | 4/1985 |
| EP | 0 371 466 A1 | 6/1990 |
| EP | 0 646 592 A | 4/1995 |
| EP | 2 001 0201.7 | 11/2002 |
| EP | 0 748 190 B1 | 7/2003 |
| EP | 3 046 928 B1 | 7/2016 |
| EP | 3106148 | 3/2018 |
| JP | H03-237557 | 10/1991 |
| JP | 2002-508330 A | 3/2002 |
| JP | 2005-523283 T | 8/2005 |
| JP | 2009-256344 A | 11/2009 |
| JP | 2010-513514 T | 4/2010 |
| JP | 2012-240917 A | 12/2012 |
| JP | 2014-224079 A | 12/2014 |
| JP | 2018-165263 A | 10/2018 |
| WO | WO-95/02408 A1 | 1/1995 |
| WO | WO-95/17895 | 7/1995 |
| WO | WO-96/03929 A1 | 2/1996 |
| WO | WO-99/30728 | 6/1999 |
| WO | WO-00/42942 | 7/2000 |
| WO | WO-00/42955 A1 | 7/2000 |
| WO | WO-01/05806 A1 | 1/2001 |
| WO | WO-01/40255 A2 | 6/2001 |
| WO | WO-02/49675 A1 | 6/2002 |
| WO | WO-02/094275 A1 | 11/2002 |
| WO | WO-02/094276 A1 | 11/2002 |
| WO | WO-02/094277 A1 | 11/2002 |
| WO | WO-02/094278 A1 | 11/2002 |
| WO | WO-02/094279 A1 | 11/2002 |
| WO | WO-02/094281 A1 | 11/2002 |
| WO | WO 03/018026 | 3/2003 |
| WO | WO-03041718 A1 * | 5/2003 ............. A61K 31/56 |
| WO | WO-2004/006936 A1 | 1/2004 |
| WO | WO-2004/019954 A1 | 3/2004 |
| WO | WO-2004/041289 A1 | 5/2004 |
| WO | WO-2004/096259 | 11/2004 |
| WO | WO-2004/103377 A1 | 12/2004 |
| WO | WO-2005/030175 A1 | 4/2005 |
| WO | WO-2005/030176 A1 | 4/2005 |
| WO | WO-2005/051400 A1 | 6/2005 |
| WO | WO-2005/105103 A2 | 11/2005 |
| WO | WO-2005/115349 A1 | 12/2005 |
| WO | WO-2005/115351 A1 | 12/2005 |
| WO | WO-2006/002937 | 1/2006 |
| WO | WO-2006/027347 A1 | 3/2006 |
| WO | WO-2006/120035 A2 | 11/2006 |
| WO | WO-2006/125800 A2 | 11/2006 |
| WO | WO-2007/081206 A1 | 7/2007 |
| WO | WO-2007/106264 A2 | 9/2007 |
| WO | WO-2008/003363 A1 | 1/2008 |
| WO | WO-2008/003432 A1 | 1/2008 |
| WO | WO-2008/156365 A1 | 12/2008 |
| WO | WO-2010/012490 A1 | 2/2010 |
| WO | WO-2010/033832 A2 | 3/2010 |
| WO | WO-2010/089078 A1 | 8/2010 |
| WO | WO-2010/149273 A1 | 12/2010 |
| WO | WO-2011/128336 A1 | 10/2011 |
| WO | WO-2012/000981 A1 | 1/2012 |
| WO | WO-2012/055840 A1 | 5/2012 |
| WO | WO-2013/012326 A1 | 1/2013 |
| WO | WO-2013/021025 A1 | 2/2013 |
| WO | WO-2013/090117 A1 | 6/2013 |
| WO | WO-2013/156329 | 10/2013 |
| WO | WO-2014/159377 A1 | 10/2014 |
| WO | WO-2014/189836 A1 | 11/2014 |
| WO | WO-2015/040051 A1 | 3/2015 |
| WO | WO-2015086643 A1 * | 6/2015 ........... A61K 31/565 |
| WO | WO-2016/053946 A1 | 4/2016 |
| WO | WO-2016/187269 A1 | 11/2016 |
| WO | WO-2016/023009 A1 | 12/2016 |
| WO | WO-2016/203006 A1 | 12/2016 |
| WO | WO-2016/203009 A1 | 12/2016 |
| WO | WO-2016/203011 A1 | 12/2016 |
| WO | WO-2016/203044 A1 | 12/2016 |
| WO | WO-2016/207298 A1 | 12/2016 |
| WO | WO-2018/024912 A1 | 2/2018 |
| WO | WO-2018/065076 A1 | 4/2018 |
| WO | WO-2019/154899 A1 | 8/2019 |
| WO | WO-2019/202141 A1 | 10/2019 |
| WO | WO-2019/202142 A1 | 10/2019 |
| WO | WO-2021/209591 A1 | 10/2021 |

OTHER PUBLICATIONS

Bosworth et al., "Depressive symptoms, menopausal status, and climacteric symptoms in women at midlife" *Psychosom. Med.* (2001) 63(4):603-608.

(56) References Cited

OTHER PUBLICATIONS

Coelingh Bennink et al., "Clinical effects of the fetal estrogen estetrol in a multiple-rising-dose study in postmenopausal women", Maturitas (2016) 91:93-100.
Harlow et al., "Executive summary of the Stages of Reproductive Aging Workshop + 10: addressing the unfinished agenda of staging reproductive aging" Menopause (2012) 19(4):1159-1168.
Heinemann et al., "International versions of the Menopause Rating Scale (MRS)" Health Qual Life Outcomes (2003) 1:28.
Heinemann et al., "The Menopause Rating Scale (MRS) scale: A methodological review". Health Qual Life Outcomes (2004) 2:45.
Heinemann et al., "The Menopause Rating Scale (MRS) as outcome measure for hormone treatment? A validation study". Health Qual Life Outcomes (2004) 2:67.
Hilditch et al., "A menopause-specific quality of life questionnaire: development and psychometric properties" Maturitas (1996) 24(3):161-175.
Notelovitz et al., "Initial 17β-Estradiol Dose for Treating Vasomotor Symptoms" Obstetrics and Gynaecology (2000) 95(5):726-731.
Portman et al., "Genitourinary syndrome of menopause: new terminology for vulvovaginal atrophy from the International Society for the Study of Women's Sexual Health and the North American Menopause Society" Menopause (2014) 21(10):1063-1068.
Radtke et al., "The Menopause-Specific quality of Life (MENQOL) Questionnaire: Psychometric Evaluation among Breast Cancer" Menopause (2011) 18(3):289-295.
Rodstrom et al., "A longitudinal study of the treatment of hot flushes: the population study of women in Gothenburg during a quarter of a century" Menopause (2002) 9(3):156-161.
Santoro, N., "Symptoms of menopause: hot flushes" Clin Obstet Gynecol (2008) 51(3):539-548.
Simon et al., "Menopausal hormone therapy for vasomotor symptoms: balancing the risks and benefits with ultra-low doses of estrogen" Expert Opin Investig Drugs (2007) 16(12):2005-2020.
Utian et al., "Comparative controlled trial of a novel oral estrogen therapy, estradiol acetate, for relief of menopause symptoms" Menopause (2005) 12(6):708-715.
U.S. Appl. No. 17/701,588, filed Mar. 22, 2022, Foidart, Jean Michel.
"Illustrated Glossary of Organic Chemistry", retrieved from http://www.chem.ucla.edu/~harding/IGOC/H/hydrate.html printed Apr. 19, 2022.
"Pharmaceutics of Biological Drugs," Editor in chief: Zhao Yingzheng, pp. 17 and 18, Zhejiang University Press (published on Jun. 30, 2011).
"Pharmaceutics," Editor in Chief: Liu Shubao, p. 153, Henan Science and Technology Press (published on Jul. 31, 2007).
Abot et al., The uterine and vascular actions of estetrol delineate a distinctive profile of estrogen receptor alpha modulation, uncoupling nuclear and membrane activation, EMBO Molecular Medicine, vol. 6, No. 10, 2014 (19 pages).
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056 (Sep. 2015).
Alam et al., "Solid dispersions: a strategy for poorly aqueous soluble drugs and technology updates," Expert Opin. Drug Deliv. vol. 9, No. 11, pp. 1420-1440 (2012).
Alexander et al., "Why consider vaginal drug administration?" Fertility and Sterility, vol. 82, No. 1 (Jul. 2004).
Andersch and Milsom, "An epidemiologic study of young women with dysmenorrhea", Am J Obstet Gynecol, 144(6), p. 655-660 (1982).
Anderson and Spencer, "Risk factors for venous thromboembolism", Circulation, vol. No. 107, 2003, pp. I-9-I-16.
Apter et al., "Bleeding pattern and cycle control with estetrol-containing combined oral contraceptives: results from a phase II, randomized, dose-finding study (FIESTA)," Contraception 94 (2016) pp. 366-373.

Apter, D. et al., "Estetrol combined with drospirenone: an oral contraceptive with high acceptability, user satisfaction, well-being and favourable body weight control", The European Journal of Contraception and Reproductive Health Care, vol. No. 22, Issue No. 4, 2017, pp. 260-267.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8, 99-217, Abstract 0333.
Bagot et al., "The effect of estrone on thrombin generation may explain the different thrombotic risk between oral and transdermal hormone replacement therapy", J Thromb Haemost., 8(8):1736-1744 (2010).
Bennink et al., "Estetrol (E4), the forgotten fetal steroid", 9th European Congress of Endocrinology Meeting Abstract No. S16,2, Endocrine Abstracts, vol. No. 14 (2007).
Bennink et al., "Estetrol review: profile and potential clinical applications," Climacteric (2008) vol. 11, Suppl. 1, pp. 47-58.
Bennink et al., "Pharmacodynamic effects of the fetal estrogen estetrol in postmenopausal women: results from a multiple-rising-dose study," (2017) Menopause 24(6), pp. 677-685.
Bennink et al., "Pharmacokinetics of the fetal estrogen estetrol in a multiple-rising-dose study in postmenopausal women," (2017) Climacteric.20(3), pp. 285-289.
Bianchi, "Estetrol: Desde Un Estrogeno Fetal Hasta El Tratamiento De La Menopausia," Rev. Chil. Obstet. Ginecol., vol. 74, No. 2, pp. 123-126 (2009).
Bird et al., "Drospirenone and non-fatal venous thromboembolism: is there a risk difference by dosage of ethinyl-estradiol?" Journal of Thrombosis and Haemostasis, vol. 11, pp. 1059-1068 (2013).
Blanco-Molina, M.A. et al., "Progestin-only contraception and venous thromboembolism", Thrombosis Research, vol. No. 129, 2012, pp. e257-e262.
Brenková et al., CHISA 2006—17th International Congress of Chemical and Process Engineering.
Bull et al., "Synthesis and structure-activity studies of 8a- and 9beta-analogues of 14,17-ethanoestradiol", J. Chem. Soc., Perkin Trans 1, 2000, pp. 1003-1013.
Callejo et al., "Effect of a low-dose oral contraceptive containing 20 microg ethinylestradiol and 150 microg desogestrel on dysmenorrhea", Contraception, 68(3), p. 183-188 (2003).
Chilukuri, D. et al., "Pharmaceutical Product Development: In Vitro-In Vivo Correlation", Informa Healthcare, Drugs and the Pharmaceutical Sciences, vol. No. 165, 2007, 216 pages.
Coelingh Bennink et al., "Ovulation inhibition by estetrol in an in vivo model" Contraception, 2008, vol. 77, pp. 186-190.
Dahlback et al., "Familial thrombophilia due to a previously unrecognized mechanism characterized by poor anticoagulant response to activated protein C: prediction of a cofactor to activated protein C", Proc Natl Acad Sci U S A., 90(3), p. 1004-1008 (1993).
Davis et al., "Oral contraceptives for dysmenorrhea in adolescent girls: a randomized trial", Obstet Gynaecol, 106(1):97-104 (2005).
De Bastos et al., "Combined oral contraceptives: venous thrombosis", Cochrane Database Syst Rev, (3):CD010813 (2014).
Dey et al., "Orodispersible tablets: A new trend in drug delivery," Journal of Natural Science, Biology, and Medicine, vol. 1, No. 1, p. 2-5, (Jul. 2010).
Dinger et al., "Effectiveness of Oral Contraceptive Pills in a Large U.S. Cohort Comparing Progestogen and Regimen", Obstet. & Gynecol., 117(1):33-40 (2011).
Dinger et al., "Oral Contraceptive Effectiveness According to Body Mass Index, Weight, Age, and Other Factors", Am. J. Obstet. Gynecol., 201:263e1-9 (2009).
Dinger et al., "Risk of venous thromboembolism and the use of dienogest- and drospirenone-containing oral contraceptives: results from a German case-control study", J Fam Plann Reprod Health Care, 36(3), 2010, pp. 123-129.
Duijkers et al., "A randomized study comparing the effect on Ovarian activity of a progestogen-only pill (POP) containing desogestrel and a new POP containing drospirenone in a 24/4 regimen", Euro. J. Contracept. & Repro. Health Care, 20(6):419-27 (2015).
Duijkers et al., "Inhibition of ovulation by administration of estetrol in combination with drospirenone or levonorgestrel: Results of a

(56) References Cited

OTHER PUBLICATIONS phase II dose-finding pilot study," The European Journal of Contraception and Reproductive Health Care (2015) vol. 20, pp. 476-489.
Elger et al., "Conception and pharmacodynamics profile of drospirenone", Steriods, 68(10):891-905 (2003).
Endrikat et al., "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235 (1995).
Erkkola et al., "Role of progestins in contraception", Acta Obstet Gynecol Scand., 84(3), pp. 207-216 (2005).
European Society of Contraception and Reproductive Health (ESC), "Estelle®; the new contraceptive pill containing the fetal estrogen estetrol (E4)", I4th Congress, 2nd Global Conference, May 4 to May 7, 2016, Switzerland.
European Society of Contraception and Reproductive Health (ESC), "New molecules, applications (and regimens)—Room Sydney—Estetrol", I4th Congress, 2nd Global Conference, May 4 to May 7, 2016, Switzerland.
Fine, P., Update on Emergency Contraception, Advances in Therapy, vol. No. 28, Issue No. 2, 2010, pp. 87-90.
Foidart, "Estelle?, Estetrol and drospirenone in oral contraception: E4 Freedom TM Phase 3 clinical study design," Presented at Eur. Soc. Contraception & Reprod. Health, 14th Cong, 2nd Global Conf. (May 5, 2016).
Foidart, "Estetrol, the first human, physiological Selective Estrogen Receptor Modulator," Presented at Eur. Soc. Contraception & Reprod. Health, 14th Cong, 2nd Global Conf. (May 5, 2016).
French, "Dysmenorrhea", Am Fam Physician, 71(2): 285-291 (2005).
Gardouh et al., "Preparation and Characterization of Mucoadhesive Buccal Film for Delivery of Meloxicam," British Journal of Pharmaceutical Research, vol. 3, No. 4, pp. 743-766 (Jun. 2013).
Ghandi et al., "BCS class IV drugs: Highly notorious candidates for formulation development," Journal of Controlled Release, vol. 248, pp. 71-95 (2017) (Available online Jan. 11, 2017).
Haque et al., "Development of polymer-bound fast-dissolving metformin buccal film with disintegrants," International Journal of Nanomedicine, vol. 10 (Suppl. I: Challenges in biomaterials research) pp. 199-205 (Oct. 2015).
Harada, T., "Dysmenorrhea and Endometriosis in Young Women," Yonago Acta medica, vol. 56, pp. 81-84 (2013).
Harel et al., "Dysmenorrhea in adolescents and young adults: an update on pharmacological treatments and management strategies," Expert Opinion on Pharmacotherapy, vol. 13 No. 15, (Sep. 2012) pp. 2157-2170, XP055389783.
Harrington et al., "Cross-sectional association of endogenous steroid hormone, sex hormone-binding globulin, and precursor steroid levels with hemostatic factor levels in postmenopausal women", J Thromb Haemost., 15(1), p. 80-90 (2017).
Hendrix and Alexander, "Primary dysmenorrhea treatment with a desogestrel-containing low-dose oral contraceptive", 66(6), p. 393-399 (2002).
International Search Report and Written Opinion on PCT Appl. Ser. No. PCT/EP2019/060220 dated Jul. 11, 2019 (10 pages) (WO2019/202141).
International Search Report dated Jul. 21, 2017 in International Application No. PCT/EP2016/076104 (WO 2018/065076).
International Search Report dated May 2, 2019 in International Application No. PCT/EP2019/052980 (WO 2019/154899).
International Search Report dated Oct. 20, 2017 in International Application No. PCT/EP2017/069908 (WO 2018/024912).
International Search Report issued in International Patent Application No. PCT/EP2014/077127, dated Feb. 3, 2015.
Jezerska, L. et al., "Particles segregation in pharmaceutical mixtures for direct tablets compression", VSB-Technical University of Ostrava, Jan. 2006, 8 pages.
Jick et al., "Risk of idiopathic cardiovascular death and nonfatal venous thromboembolism in women using oral contraceptives with differing progestagen components", Lancet, 346(8990), 1995, p. 1589-1593.
Kluft, "Effects on estrogenic and haemostatic variables of estetrol in combination with drospirenone," Presented at Eur. Soc. Contraception & Reprod. Health, 14th Cong, 2nd Global Conf. (May 5, 2016).
Kluft, C. et al., "Reduced hemostatic effects with drospirenone-based oral contraceptives containing estetrol vs. ethinyl estradiol", Contraception, vol. No. 95, Issue No. 2, 2016, pp. 140-147.
Lan, Y., "A New Excipient for Fast Disintegrating Oral Dosage Forms," (BASF) 2008.
Lianmei, L et al., "Major research advances in estetrol," (2009) J Reprod Med, vol. 18(3), pp. 305-308.
Lidegaard et al., "Hormonal contraception and risk of venous thromboembolism: national follow-up study," BMJ, 339:b2890, 2009, pp. 1-8.
Lidegaard et al., "Risk of venous thromboembolism from use of oral contraceptives containing different progestagens and oestrogen doses: Danish cohort study, Sep. 2001", BMJ, 2011, 343:d6423, 15 pages.
Mawet et al., "Unique effects on hepatic function, lipid metabolism, bone and growth endocrine parameters of estetrol in combined oral contraceptives," The European Journal of Contraception and Reproductive Health Care, (2015) vol. 20, pp. 463-475.
Meeting of the Committee for Medicinal Products for Human Use (CHMP) in Mar. 2021, https://www.aemps.gob.es/informa/boletines-aemps/boletin-chmp/2021-boletinchmp/reunion-del-comite-de-medicamentos-de-uso-humano-chmp-de-marzo-2021/.
Meulenbroeks et al: "21+7 day versus 24+4 day monophasic regimens of combined oral contraceptives for contraception (Protocol)", Cochrane database of systematic reviews, Issue 7, art. No. CD011781, 2015.
Nath and Sitruk-Ware, "Pharmacology and clinical applications of selective estrogen receptor modulators", Climacteric, vol. No. 12, Issue No. 3, Jun. 2009, pp. 188-205.
Nillius et al., "Plasma Levels of Progesterone After Vaginal, Rectal, or Intramuscular Administration of Progesterone," American Journal of Obstetrics and Gynecology, vol. 110, No. 4 (1971).
Odlind et al., "Can changes in sex hormone binding globulin predict the risk of venous thromboembolism with combined oral contraceptive pills?", Acta Obstet. Gynecol. Scand., 81(6), p. 482-490.
Office Action dated Dec. 15, 2021, in Dominican patent application No. P2019-0108.
Office Action dated Dec. 23, 2019, in Israeli Application No. 256283.
Office Action dated Feb. 11, 2020 in Colombian Application No. NC2017/0012766.
Office Action dated Feb. 18, 2020 in Indian Application No. 201817001353.
Office Action dated Feb. 6, 2020 in Chinese Application No. 201680035627.8.
Office Action dated Jan. 15, 2020, in Israeli Application No. 256282.
Office Action dated Mar. 19, 2020, in Chilean Application No. 201901152.
Office Action dated Mar. 19, 2019, in Colombian application No. NC2017/0012766.
Office Action dated May 19, 2020 in Israeli Application No. 256282.
Office Action dated May 19, 2020 in Israeli Application No. 256283.
Osayande, A. et al., "Diagnosis and Initial Management of Dysmenorrhea", American Family Physician, vol. No. 89, Issue No. 5, Mar. 1, 2014, pp. 341-346.
Perie et al., "Controlling Drug Delivery," Pharmaceutics: Drug Delivery and Targeting pp. 8-9 (Pharm. Press, 2d ed., 2012).
Pinkerton, JoAnn V., https://www.msdmanuals.com/esdo/professional/ginecolog%C3%ADa-yobstetricia/anomal%C3%ADas-menstruales/dismenorrea (Dec. 2020).
Poort et al., "A common genetic variation in the 3'-untranslated region of the prothrombin gene is associated with elevated plasma prothrombin levels and an increase in venous thrombosis", Blood, 88(10), p. 3698-3703 (1996).

(56) References Cited

OTHER PUBLICATIONS

Prandoni, P. et al., "An Association between Atherosclerosis and Venous Thrombosis", The New England Journal of Medicine, vol. No. 348, Issue No. 15, Apr. 10, 2003, pp. 1435-1441.
Prince et al., "Phase II Clinical Study of BC-3781, a Pleuromutilin Antibiotic, in Treatment of Patients with Acute Bacterial Skin and Skin Structure Infections", Antimicrobial Agents and Chemotherapy, US, (May 2013), vol. 57, No. 5, doi:10.1128/AAC.02106-12, ISSN 0066-4804, pp. 2087-2094, XP055287601.
Proctor and Farquhar, "Dysmenorrhoea", Clin Evid, 9, p. 1994-2013 (2003).
Rosenbaum et al., "Inhibition of ovulation by a novel progestogen (drospirenone) alone or in combination with ethinylestradiol", Euro. J. Contracept. & Repro. Health Care, 5(1):14-24 (2000).
Rosing et al., "Oral contraceptives and venous thrombosis: different sensitivities to activated protein C in women using second- and third-generation oral contraceptives", Br J Haematol., 97(1), p. 233-238.
Sarfaraz, Handbook of Pharmaceutical Manufacturing Formulations Compressed Solid Products, Second edition, vol. 1, 2009.
Savjani et al., "Drug solubility: importance and enhancement techniques", ISRN Pharm., 2012: 195727.
Shulman, "Estelle, Estetrol: changing hormones in advancing oral contraception," Presented at Eur. Soc. Contraception & Reprod. Health, 14th Cong, 2nd Global Conf. (May 5, 2016).
Sidney et al., "Recent combined hormonal contraceptives (CHCs) and the risk of thromboembolism and other cardiovascular events in new users", Contraception, 87(1), p. 93-100 (2013).
Simoni et al., "The Discovery of Estrone, Estriol, and Estradiol and the Biochemical Study of Reproduction. The Work of Edward Adelbert Doisy", J. Biol. Chem, vol. 277, No. 28, e17, 2002, 2 pages.
Spitzer et al., "Third generation oral contraceptives and risk of venous thromboembolic disorders: an international case-control study. Transnational Research Group on Oral Contraceptives and the Health of Young Women", BMJ, 312(7023), p. 83-88 (1996).
Strickley et al., "Solubilizing Excipients in Oral and Injectable Formulations," Pharmaceutical Research, Springer New York LLC, US, vol. 21, No. 2,(Feb. 1, 2004), doi:10.1023/B:PHAM.0000016235. 32639.23, ISSN 0724-8741, pp. 201-230, XP009035738.
Strowitzki et al., "Efficacy of ethinylestradiol 20 ug/drospirenone 3 mg in a flexible extended regimen in women with moderate-to-severe primary dysmenorrhea: an open-label, multicenter, ramdomized, controlled study," J. Fam. Plann. Reprod. Health Care (2012) vol. 38, pp. 94-101.
Sundell et al., "Factors influencing the prevalence and severity of dysmenorrhoea in young women.", Br J Obstet Gynaecol, 97(7), p. 588-594.
Tchaicovski and Rosing, "Mechanisms of estrogen-induced venous thromboembolism", Thromb Res., 126(1):5-11.
The American College of Obstetricians and Gynecologists, "Committee Opinion No. 540: Risk of Venous Thromboembolism Among Users of Drospirenone-Containing Oral Contraceptive Pills", Nov. 2012, 4 pages.
The European Agency for the Evaluation of Medicinal Products, "CPMP Public Assessment Report—Combined oral contraceptives and venous thromboembolism", Sep. 2001, 7 pages.
Tulchinsky D et al. "Plasma Estetrol as an Index of Fetal Well-being," Clin Edoctrinol Metab, vol. 40, pp. 560-567 (1975).
U.S. Department of Health & Human Services—National Institutes of Health—National Center for Advancing Translational Sciences, "Estetrol Monohydrate", retrieved from https://drugs.ncats.io/substance/KC3GI9UM9V (First Approved in 2001).
U.S. Department of Health and Human Services—Food and Drug Administration—Center for Drug Evaluation and Research (CDER), "SUPAC: Manufacturing Equipment Addendum: Guidance for Industry", Pharmaceutical Quality/CMC, Dec. 2014, 33 pages.
Visser et al., "Clinical applications for estetrol," Journal of Steroid Biochemistry and Molecular Biology 114 (2009) 85-89.
Vlieg et al., "The venous thrombotic risk of oral contraceptives, effects of oestrogen dose and progestogen type: results of the MEGA case-control study", BMJ, 2009, 339:b2921, 8 pages.
Williams et al., "Strategies to address low drug solubility in discovery and development," (2013) Pharmacological Reviews, vol. 65(1), pp. 416-445.
Winkler et al., "Cycle control, quality of life and acne with two low-dose oral contraceptives containing 20 microg ethinylestradiol", Contraception, 96(6), 2004, pp. 469-476.
Wong et al., "Oral contraceptive pill as treatment for primary dysmenorrhoea", Cochrane Database Syst Rev., CD002120, 2009.
WTO, "Venous thromboembolic disease and combined oral contraceptives: results of international multicentre case-control study", Lancet, 346(8990), p. 1575-1582 (1995).
Ylikorkala and Dawood, "New concepts in dysmenorrhea", Am J Obstet Gynecol, 130(7), 1978, p. 833-847.
Zhang and Wan Po, "Efficacy of minor analgesics in primary dysmenorrhoea: a systematic review", Br J Obstet Gynaecol, vol. 130, Issue No. 7, Jul. 1998, pp. 780-789.

\* cited by examiner

COMPOUNDS AND THEIR USES FOR ALLEVIATING MENOPAUSE-ASSOCIATED SYMPTOMS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including PCT Application No. PCT/EP2019/060221, filed Apr. 19, 2019, and EP Application No. 18168234.5, filed Apr. 19, 2018, EP Application No. 18174985.4, filed May 30, 2018 and EP Application No. 19150421.6, filed Jan. 4, 2019.

FIELD OF THE INVENTION

The present invention relates to hormone replacement therapy, to the associated compounds and to the associated packaging units, for alleviating menopause-associated symptoms which is based on the administration to a female mammal of an estetrol component at a specific daily dose, optionally in combination with a progestogenic component.

As further detailed herein, the therapy displays statistically significant efficacy combined with a favourable profile for side effects compared to currently available methods for alleviating menopause-associated symptoms.

BACKGROUND ART

Hormone replacement therapy (HRT) is used to describe either unopposed oestrogen use (for women who have undergone hysterectomy) or combined oestrogen-progestin therapy (for women still having a uterus). The goal of HRT is to relieve menopausal symptoms, most importantly vasomotor symptoms (VMS), such as hot flushes. Other diseases and symptoms associated with perimenopause and menopause that respond to oestrogen therapy include osteoporosis, vaginal atrophy, and sleep disturbances (when related to hot flushes).

VMS occur most often in the late menopausal transition and early post-menopause. VMS are the most significant menopausal complaints. Estimates suggest that about 75% of women who are more than 50 years old will suffer from hot flushes (Utian et al., 2005, *"Comparative controlled trial of a novel oral estrogen therapy, estradiol acetate, for relief of menopause symptoms"* Menopause 12(6): 708-715). Most experience hot flushes for about two years, although around 10% suffer for more than 10 years (Rodstrom et al., 2002, *"A longitudinal study of the treatment of hot flushes: the population study of women in Gothenburg during a quarter of a century"* Menopause 9(3): 156-161). VMS can contribute towards physical and psycho-social impairment, with a consequent reduction in quality of life, and are one of the main reasons why women may seek medical care for the menopause (Santoro, 2008, *"Symptoms of menopause: hot flushes"* Clin Obstet Gynecol 51(3): 539-548).

The epithelial linings of the vagina and urethra are very sensitive to oestrogen, and oestrogen deficiency leads to thinning both epithelia. This results in vulvovaginal atrophy (VVA) and urinary complaints, causing symptoms of vaginal dryness, itching, dyspareunia, dysuria, urinary frequency and an increased risk of recurrent urinary infections. In early 2014, the International Society for the Study of Women's Sexual Health (ISSWSH) and the North American Menopause Society (NAMS) endorsed the new terminology "genitourinary syndrome of menopause (GSM)" to replace the VVA terminology. The rationale for using this new terminology was that VVA term was too restrictive whereas GSM was a more comprehensive term that includes symptomatic VVA as well as lower urinary tract symptoms related to low oestrogen levels (Portman et al., 2014, *"Genitourinary syndrome of menopause: new terminology for vulvovaginal atrophy from the International Society for the Study of Women's Sexual Health and the North American Menopause Society"* Menopause 21(10): 1063-1068). Note that the GSM terminology has not yet been adopted in guidance for industry issued by the FDA and EMA, therefore the VVA terminology will be used herein.

Oestrogen therapy remains the gold standard for relief of menopausal symptoms, in particular VMS. All routes of administration appear to be equally effective for symptom relief, but their metabolic effects differ. Oestrogens should be administered continuously; past regimens where oestrogen was administered day 1 to day 25 of the calendar month are considered to be obsolete. Women will often get VMS during the days off, and there is no known advantage to stopping for several days each month.

With current HRT, all women with an intact uterus need a progestin in addition to oestrogen to prevent endometrial hyperplasia—and subsequent carcinoma—which occurs after as little as 6 months of oestrogen therapy. The progestin may be administered continuously or sequentially (e.g., 10 to 14 days each month or for 14 days every 3 months).

Oestrogen therapy is the most consistently effective treatment used in the US and Europe for menopausal VMS. Following the safety issues reported in the primary Women's Health Initiative publications (Anderson et al., 2004, *"Effects of conjugated equine estrogen in postmenopausal women with hysterectomy: the Women's Health Initiative randomized controlled trial"* JAMA 291(14): 1701-1712) and with continued subject requests for treatment, a challenge to clinicians has been to identify the lowest effective dose of oestrogen for alleviating menopausal symptoms (Simon et al., 2007, *"Menopausal hormone therapy for vasomotor symptoms: balancing the risks and benefits with ultra-low doses of estrogen"* Expert Opin Investig Drugs 16(12): 2005-2020). In addition, it is a challenge to develop a safer oestrogen than those currently used.

In a 2016 publication, Coelingh Bennink et al; (*"Clinical effects of the fetal estrogen estetrol in a multiple-rising-dose study in postmenopausal women"*, Maturitas, 2016 September; 91:93-100) report a partly randomized, open-label, multiple-rising-dose study in 49 postmenopausal women who received either 2 mg estetrol or 2 mg estradiol-valerate per day for 28 days (randomized part of the study) followed by dose-escalation at 10, 20 and 40 mg estetrol per day (non-randomized part of the study). The authors compared the efficacy of estradiol-valerate (2 mg) and only two doses of estetrol (2 and 10 mg) on the relief of hot flushes on subjects with >35 hot flushes per week at screening (note a. to Table 1). The authors report a decrease in the mean number of hot flushes and sweating already with the 2 mg estetrol per day dose, while at the same time endometrial thickness was found to be stable in the 2 mg estetrol group but increasing in the 10 mg estetrol group (abstract).

From this study, since the authors did not measure VMS in the 20 mg and 40 mg estetrol groups, it is apparent to the skilled person that the authors considered only the lower doses (2 mg and 10 mg) to be suitable for the management of VMS. Further, the skilled person learns that a daily dose of 2 mg estetrol is as effective as a daily dose of 10 mg estetrol at decreasing the number of hot flushes per day (see for example FIG. 3 in Coelingh Bennink et al., Maturitas, 2016). In addition, the publication teaches the skilled person that the 2 mg daily dose does not alter endometrial thickness while the 10 mg daily dose has an important effect on endometrial thickness (see for example FIG. 2 in Coelingh Bennink et al., 2016). The skilled person would thus conclude that the Minimal Effective Dose of estetrol for the treatment of VMS is 2 mg per day.

SUMMARY OF THE INVENTION

Against this background, the present inventors have now surprisingly found that the Minimal Effective Dose of estetrol for the alleviation of VMS in perimenopausal and postmenopausal women is of about 15 mg daily.

The determination of the Minimal Effective Dose indeed revolves around a number of parameters which take into account not only the mean number of VMS per day (as was done by Coelingh Bennink et al in Maturitas, 2016), but also the severity of VMS, and also a weekly weighted score, as further defined herein.

Thus, in terms of efficacy, it was surprisingly found that a daily dose of 15 mg was required to obtain a definite effect on VMS.

Furthermore, the Minimal Effective Dose is set taken due account of treatment-associated side effects as reflected for example in the number of patients leaving the study in each group, or in the number of biopsies which had to be performed in each group.

In this regard, it was unexpected to observe, from parameters such as the total number of adverse events, the number of biopsies, or the number of patients leaving the study, a better safety profile for a patient group treated with a daily dose of 15 mg of estetrol than for a patient group treated with a lower daily dose of 10 mg of estetrol.

In the following numbered paragraphs 1 to 15, embodiments of the invention are described.

1. A composition for use in alleviating menopause-associated symptoms, wherein said composition comprises an estetrol component and wherein said composition is administered at a daily amount equivalent to about 15 mg of estetrol.
2. A composition for use in alleviating vasomotor symptoms selected from hot flashes, sweating attacks, night sweats, chills, increased perspiration, palpitations and combinations thereof, wherein said composition comprises an estetrol component and wherein said composition is administered at a daily amount equivalent to about 15 mg of estetrol.
3. A composition for use in alleviating emotional aspects of the menopausal transition selected from depression, irritability, mood changes, insomnia, sleep disturbance, anxiety, nervous tension and combinations thereof, wherein said composition comprises an estetrol component and wherein said composition is administered at a daily amount equivalent to about 15 mg of estetrol.
4. A composition for use in alleviating physiological aspects of the menopausal transition selected from joint pain, loss of bone density, urinary tract infections, urinary incontinence, dryness of the vagina, uterine prolapse, changes in skin texture, weight gain, dyspareunia, cardiovascular diseases, diabetes and combinations thereof, wherein said composition comprises an estetrol component and wherein said composition is administered at a daily amount equivalent to about 15 mg of estetrol.
5. A composition for use in reducing VMS frequency, VMS severity, hot flush weekly weighted score, dryness of the vagina, dyspareunia and combinations thereof, or for use in improving Quality of Life according to the MRS and/or the MENQOL questionnaires, wherein said composition comprises an estetrol component and wherein said composition is administered at a daily amount equivalent to about 15 mg of estetrol.
6. A composition for use in improving Quality of Life according to the MRS and/or the MENQOL questionnaires in a perimenopausal subject, wherein said composition comprises an estetrol component and wherein said composition is administered at a daily amount equivalent to about 15 mg of estetrol.
7. The composition for use according to any one of paragraphs 1-6 above wherein the composition is administered daily for at least 1, at least 2, at least 4, at least 6, at least 12 weeks.
8. The composition for use of any one of paragraphs 1-7 wherein a second composition comprising a progestogenic component is additionally used.
9. The composition for use of paragraph 8 wherein said progestogenic component is selected from drospirenone, progesterone and dydrogesterone.
10. The composition for use of paragraph 8 wherein progesterone is administered at a daily dose of from 50 mg to 200 mg.
11. The composition for use of any one of paragraphs 1-7 wherein a second composition comprising bazedoxifene is additionally used.
12. A composition for use according to any one of paragraphs 8-11 wherein said second composition comprising a progestogenic component or bazedoxifene is the same as the composition comprising the estetrol component.
13. A composition for use according to any one of paragraphs 1-12 wherein the estetrol component is estetrol, preferably estetrol monohydrate.
14. A composition for use according to any of the preceding paragraphs wherein the composition is formulated as an oral dosage unit.
15. The composition for use according to paragraph 14 wherein the oral dosage unit is formulated to correspond to a daily dosage unit.

In the following numbered paragraphs 16 to 30, additional embodiments of the invention are described.

16. A method of alleviating menopause-associated symptoms which comprises administration of a composition comprising an estetrol component at a daily amount equivalent to about 15 mg of estetrol.
17. A method of alleviating vasomotor symptoms selected from hot flashes, sweating attacks, night sweats, chills, increased perspiration, palpitations and combinations thereof, which comprises administration of a composition comprising an estetrol component at a daily amount equivalent to about 15 mg of estetrol.
18. A method of alleviating emotional aspects of the menopausal transition selected from depression, irritability, mood changes, insomnia, sleep disturbance, anxiety, nervous tension and combinations thereof, which comprises administration of a composition comprising an estetrol component at a daily amount equivalent to about 15 mg of estetrol.
19. A method of alleviating physiological aspects of the menopausal transition selected from joint pain, loss of bone density, urinary tract infections, urinary incontinence, dryness of the vagina, uterine prolapse, changes in skin texture, weight gain, dyspareunia, cardiovascular diseases, diabetes and combinations thereof, which comprises administration of a composition comprising an estetrol component at a daily amount equivalent to about 15 mg of estetrol.
20. A method of reducing VMS frequency, VMS severity, hot flush weekly weighted score, dryness of the vagina, dyspareunia and combinations thereof, or of improving Quality of Life according to the MRS and/or the MENQOL questionnaires, which comprises administration of a composition comprising an estetrol component at a daily amount equivalent to about 15 mg of estetrol.
21. A method of improving Quality of Life according to the MRS and/or the MENQOL questionnaires in a perimenopausal subject, which comprises administration of a composition comprising an estetrol component at a daily amount equivalent to about 15 mg of estetrol.
22. The method according to any one of paragraphs 16-21 above wherein the composition is administered daily for at least 1, at least 2, at least 4, at least 6, at least 12 weeks.
23. The method according to any one of paragraphs 16-22 wherein a second composition comprising a progestogenic component is additionally administered.
24. The method according to paragraph 23 wherein said progestogenic component is selected from drospirenone, progesterone and dydrogesterone.
25. The method according to paragraph 23 wherein progesterone is administered at a daily dose of from 50 mg to 200 mg.
26. The method according to any one of paragraphs 16-22 wherein a second composition comprising bazedoxifene is additionally administered.
27. The method according to any one of paragraphs 23-26 wherein said second composition comprising a progestogenic component or bazedoxifene is the same as the composition comprising the estetrol component.
28. The method according to any one of paragraphs 16-27 wherein the estetrol component is estetrol, preferably estetrol monohydrate.
29. The method according to any of the preceding paragraphs wherein the composition is formulated as an oral dosage unit.
30. The method according to paragraph 29 wherein the oral dosage unit is formulated to correspond to a daily dosage unit.

In the following numbered paragraphs 31 to 45, additional embodiments of the invention are described.

31. Use of an effective amount of an estetrol component in the manufacture of a composition for alleviating menopause-associated symptoms, wherein the estetrol component is used at a daily amount equivalent to about 15 mg of estetrol.
32. Use of an effective amount of an estetrol component in the manufacture of a composition for alleviating vasomotor symptoms selected from hot flashes, sweating attacks, night sweats, chills, increased perspiration, palpitations and combinations thereof, wherein the estetrol component is used at a daily amount equivalent to about 15 mg of estetrol.
33. Use of an effective amount of an estetrol component in the manufacture of a composition for alleviating emotional aspects of the menopausal transition selected from depression, irritability, mood changes, insomnia, sleep disturbance, anxiety, nervous tension and combinations thereof, wherein the estetrol component is used at a daily amount equivalent to about 15 mg of estetrol.
34. Use of an effective amount of an estetrol component in the manufacture of a composition for alleviating physiological aspects of the menopausal transition selected from joint pain, loss of bone density, urinary tract infections, urinary incontinence, dryness of the vagina, uterine prolapse, changes in skin texture, weight gain, dyspareunia, cardiovascular diseases, diabetes and combinations thereof, wherein the estetrol component is used at a daily amount equivalent to about 15 mg of estetrol.
35. Use of an effective amount of an estetrol component in the manufacture of a composition for reducing VMS frequency, VMS severity, hot flush weekly weighted score, dryness of the vagina, dyspareunia and combinations thereof, or for improving Quality of Life according to the MRS and/or the MENQOL questionnaires, wherein the estetrol component is used at a daily amount equivalent to about 15 mg of estetrol.
36. Use of an effective amount of an estetrol component in the manufacture of a composition for improving Quality of Life according to the MRS and/or the MENQOL questionnaires in a perimenopausal subject, wherein the estetrol component is used at a daily amount equivalent to about 15 mg of estetrol.
37. The use according to any one of paragraphs 31-36 above wherein the composition is administered daily for at least 1, at least 2, at least 4, at least 6, at least 12 weeks.
38. The use according to any one of paragraphs 31-37 wherein a second composition comprising a progestogenic component is additionally administered.
39. The use according to paragraph 38 wherein said progestogenic component is selected from drospirenone, progesterone and dydrogesterone.
40. The use according to paragraph 38 wherein progesterone is administered at a daily dose of from 50 mg to 200 mg.
41. The use according to any one of paragraphs 31-37 wherein a second composition comprising bazedoxifene is additionally administered.
42. The use according to any one of paragraphs 38-41 wherein said second composition comprising a progestogenic component or bazedoxifene is the same as the composition comprising the estetrol component.
43. The use according to any one of paragraphs 31-42 wherein the estetrol component is estetrol, preferably estetrol monohydrate.
44. The use according to any of the preceding paragraphs wherein the composition is formulated as an oral dosage unit.
45. The use according to paragraph 44 wherein the oral dosage unit is formulated to correspond to a daily dosage unit.

In the following numbered paragraphs 46 to 53, additional embodiments of the invention are described.

46. A packaging unit comprising at least 14, preferably at least 21, even more preferably at least 28, containers for holding separately packaged and individually removable daily solid oral dosage forms, wherein each container comprises at least one daily solid oral dosage form comprising about 15 mg of estetrol.
47. The packaging unit according to paragraph 46, wherein the packaging unit additionally comprises at least 10, preferably 12, more preferably 14, additional containers for holding separately packaged and individually removable daily, preferably solid, oral dosage forms, wherein each additional container comprises at least one daily, preferably solid, oral dosage form comprising a progestogenic component.

48. The packaging unit according to paragraph 47, wherein each of the additional containers for holding the dosage forms comprising the progestogenic component are individually visually arranged next to a container holding a solid dosage form comprising estetrol when these two solid dosage forms have to be administered on the same day.

49. The packaging unit according to paragraphs 47 or 48, wherein said progestogenic component is selected from drospirenone, progesterone and dydrogesterone.

50. The packaging unit according to paragraph 49, wherein said progestogenic component is progesterone and wherein each said additional containers comprises at least one daily oral dosage form comprising about 200 mg of progesterone.

51. The packaging unit according to paragraph 46, wherein the packaging unit additionally comprises the same number of additional containers for holding separately packaged and individually removable daily, preferably solid, oral dosage forms, wherein each additional container comprises at least one daily, preferably solid, oral dosage form comprising a progestogenic component, preferably wherein said progestogenic component is selected from drospirenone, progesterone and dydrogesterone, even more preferably wherein said progestogenic component is progesterone and wherein said additional container comprises at least one daily oral dosage form comprising about 100 mg of progesterone.

52. The packaging unit according to paragraph 46, wherein at least 10, preferably 12, more preferably 14, of said daily solid oral dosage forms additionally comprises a progestogenic component.

53. The packaging unit according to paragraph 46, wherein each said daily solid oral dosage form additionally comprises a progestogenic component.

The skilled person will understand that the embodiments described in numbered paragraphs 47 to 53 may equivalently be presented as a kit-of-parts containing a first packaging unit, e.g. a blister pack, containing the daily oral dosage units comprising the estetrol component, and a second, distinct, packaging unit, e.g. a second, distinct, blister pack, containing the daily oral dosage units comprising the progestogenic component.

The skilled person will additionally know that, within the scope of the present invention, each packaging unit, e.g. blister pack, may be numbered or otherwise marked.

Within the scope of the invention, each packaging unit may be a sealed blister pack with a cardboard, paperboard, foil plastic backing and enclosed in a suitable cover.

In a particular embodiment of the invention the packaging unit comprises 28 containers or a multiple of 28 containers, such as 2 to 12 multiple of 28 containers.

DETAILED DESCRIPTION OF THE INVENTION

Definitions

The term "estetrol component", as used throughout this document, encompasses substances selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component contained in the dosage unit is estetrol monohydrate.

The term "estetrol" as used herein refers to 1,3,5 (10)-estratrien-3,15alpha,16alpha,17beta-tetrol or 15alpha-hydroxyestriol as well as hydrates of estetrol, e.g. estetrol monohydrate.

The term "progestogenic component" is defined as a substance that is capable of triggering a progestogenic response in vivo or a precursor which is capable of liberating such a substance in vivo. Usually progestogenic components are capable of binding to a progestogen receptor.

In the context of the present invention, other compounds may be used in conjunction with the estetrol component for administering to women who have a uterus. Selective Estrogen Receptor Modulators (SERMs) defines a category of such compounds, which are contemplated as useful complements to the estetrol component in the methods of the invention. A preferred SERM for use in the context of the present invention is bazedoxifene.

In the methods and compositions further described herein, it has to be understood that when reference is made to a "progestogenic component", such reference includes SERMs and in particular bazedoxifene.

"About" as used herein referring to a measurable value such as a parameter, an amount, a temporal duration, and the like, is meant to encompass variations of +/−10% or less, more preferably +/−5% or less, even more preferably +/−1% or less of and from the specified value, in so far such variations are appropriate to perform in the disclosed invention. However, it is to be understood that the value to which the modifier "about" refers is itself also specifically disclosed.

The term "an effective amount" refers to an amount necessary to obtain a physiological effect. The physiological effect may be achieved by one dose or by repeated doses.

The term "perimenopause" as used herein (also in the context of "perimenopausal women" and "perimenopausal subject" and the like) refers to a period of life which begins approximately three to four years prior to menopause and ends one year after the final menstrual period. Perimenopause is characterized by persistent irregular menstrual cycles, extreme fluctuations in hormonal levels, frequent anovulation and the appearance of VMS (for reference: Harlow et al., *Menopause*, Vol. 19, No. 4, 2012, *"Executive summary of the Stages of Reproductive Aging Workshop+10: addressing the unfinished agenda of staging reproductive aging"*—see in particular FIG. 2 therein). During this transition period, the emphasis of clinical care changes. Although women still need effective contraception during perimenopause, issues including loss of bone mineral density, menstrual cycle changes, and vasomotor instability also need to be addressed. A significant number of women also experience depressive symptoms, such as mood swings, irritability, and poor concentration (Bosworth et al., *Psychosom Med.*, 2001, July-August; 63(4):603-8, *"Depressive symptoms, menopausal status, and climacteric symptoms in women at midlife"*).

The term "postmenopause" as used herein (also in the context of "postmenopausal women" and "postmenopausal subject" and the like) covers firstly spontaneous post-menopausal women, i.e. women who have encountered natural menopause defined as the permanent cessation of menstrual periods, determined retrospectively after a woman has experienced 12 months of amenorrhea without any other obvious pathological or physiological cause. It occurs at a median age of 51.4 years in normal women and is a reflection of complete, or near complete, ovarian follicular depletion, with resulting hypoestrogenemia (with estradiol levels often below 20 pg/mL) and high follicle-stimulating hormone (FSH level >40 IU/L) concentrations. The term "postmenopause" also includes menopause as the consequence of premature ovarian failure, surgery (ovariectomy for example), chemotherapy or radiotherapy for cancer, and certain diseases (for example, infections or hypothyroidism).

The term "VMS" as used herein (alternatively in its non-abbreviated form, "vasomotor symptoms") corresponds to thermo-regulatory disturbances characteristic of menopause. VMS includes hot flashes (also sometimes spelled "hot flushes"), sweating attacks such as night sweats, chills and increased perspiration, and palpitations. VMS are episodes of profuse heat accompanied by sweating and flushing, experienced predominantly around the head, neck, chest, and upper back. As further defined below, VMS are classified into mild, moderate and severe categories.

The terms "Menopause-associated symptoms", as used herein, is used to describe VMS as defined above, but also includes the emotional aspects of the menopausal transition (including, but not limited to, depression, irritability, mood changes, insomnia, sleep disturbance, anxiety and nervous tension) and the physiological aspects of the menopausal transition (including, but not limited to joint pain, loss of bone density, urinary tract infections, urinary incontinence, dryness of the vagina, uterine prolapse, changes in skin texture, weight gain and dyspareunia, as well as cardiovascular diseases and diabetes).

As used herein, the terms "Quality of Life" (and the abbreviation "QoL") refers to a parameter which can be assessed, for example, by using questionnaires, such as, by way of example and not limitation, the "Menopause Rating Scale" questionnaire (Heinemann et al., 2003, *"International versions of the Menopause Rating Scale (MRS)"* Health Qual Life Outcomes 1: 28; Heinemann et al., 2004, *"The Menopause Rating Scale (MRS) scale: A methodological review"*. Health Qual Life Outcomes 2: 45; Heinemann et al., 2004, *"The Menopause Rating Scale (MRS) as outcome measure for hormone treatment? A validation study"*. Health Qual Life Outcomes 2:67; as further detailed below in Example 1 Section C.) or the MENQOL questionnaire (The Menopause-specific Quality of Life (MENQOL) questionnaire, Hilditch et al.; Maturitas 1996; *A menopause-specific quality of life questionnaire: development and psychometric properties;* 24(3); p. 161-175).

As used herein, "BMI" (or "Body Mass Index" in its non-abbreviated form refers to an index relating to weight and height of a subject, which is calculated by dividing the subject's weight in kilograms by the subject's height in meters squared. A BMI of 27.3 or more classifies the female subject as "overweight" while a BMI of 30 or more classifies the subject as "obese".

Determination of the Minimum Effective Dose

To determine the Minimum Effective Dose (MED), firstly the selection criteria required that patients presented at least 7 moderate to severe VMS/day or at least 50 moderate to severe VMS/week in the week preceding randomization. Secondly, a placebo group was included in a double-blind fashion. Thirdly, the total patient number was such that statistical significance could be obtained between separate arms of the study. Fourthly, the absolute change from baseline in weekly frequency of moderate to severe VMS was taken into account. An analysis of covariance (ANCOVA) was performed based on the untransformed change in weekly frequency of moderate to severe VMS from baseline. Finally, the change in severity from baseline was evaluated. For this, the Severity Scoring System of VMS was documented by the subjects as follows:

a score of Mild (1) for a sensation of heat without sweating;

a score of Moderate (2) for a sensation of heat with sweating/the subject is able to continue activity; and a score of Severe (3) for a sensation of heat with sweating/ which causes cessation of activity.

In addition, a severity score of zero was attributed to the patients who have experienced a 100% VMS relief during a given week.

From these score records, the severity at baseline was calculated by taking into account only moderate and severe VMS, such that the total number of moderate VMS during the 7 days of the baseline week was multiplied by 2 and added to the total number of severe VMS during the 7 days of the baseline week multiplied by 3. This total was then divided by the total number of moderate and severe VMS during the baseline week.

The severity at weeks 4 and 12 was calculated using the following formula for each of these weeks:

the number of mild VMS during 7 days multiplied by 1;

the number of moderate VMS during 7 days multiplied by 2;

the number of severe VMS during 7 days multiplied by 3. and adding the 3 resulting numbers together before dividing this total by the total number of mild, moderate and severe VMS during the 7 days of the week.

This method was used to generate the data included in Example 1 further below, under section A. b) "VMS Severity".

In an alternative embodiment, the VMS Severity is assessed as follows: the severity at baseline is also calculated by taking into account only moderate and severe VMS, such that the total number of moderate VMS during the 7 days of the baseline week is multiplied by 2 and added to the total number of severe VMS during the 7 days of the baseline week multiplied by 3. This total is then divided by the total number of moderate and severe VMS during the baseline week.

The severity at weeks 4 and 12, however, is calculated using the following formula for each of these weeks:

the number of moderate VMS during 7 days multiplied by 2;

the number of severe VMS during 7 days multiplied by 3. and adding the 2 resulting numbers together before dividing this total by the total number of moderate and severe VMS during the 7 days of the week.

In another embodiment, the severity score can be calculated according to the method described in Archer et al, 2014 (A randomized, double-blind, placebo-controlled study of the lowest effective dose of drospirenone with 17A-estradiol for moderate to severe vasomotor symptoms in postmenopausal women; Menopause, 2014; 21(3); p. 227-235). According to this method, a daily severity score is calculated using the following formula for each day during 7 days the number of moderate VMS during 1 day is multiplied by 2;

the number of severe VMS during 1 day is multiplied by 3;

the 2 resulting numbers are added together;

the addition result is in turn divided by the total number of VMS during the same day (moderate and severe).

The same formula is applied during 7 consecutive days, the 7 resulting numbers are summed together and divided by 7 to calculate the "weekly mean daily severity" score of moderate to severe VMS.

Further, the terms "Hot Flush Weekly Weighted Score", as used herein, corresponds to a score taking into account frequency and severity which is calculated by using the severity score (as calculated above): [(1× No. of mild VMS)+(2× No. of moderate VMS)+(3× No. of severe VMS)] during a 7 day period.

Such a weighted score was for example used by Notelovitz et al. ("*Initial 17β-Estradiol Dose for Treating Vasomotor Symptoms*"; Obstetrics and Gynaecology, Vol. 95(5), May 2000, p. 726-731). This score was used to generate the data included in Example 1 further below, under section A. c) "Hot Flush Weekly Weighted Score".

In alternative embodiments, any combination of the above described methods maybe employed to evaluate the weekly severity and/or frequency of VMS.

Hormone Replacement Therapy

The present therapy usually employs continuous administration of the estetrol component during a period of at least 10 days, preferably of at least 20 days.

When the present therapy is administered to a patient who has undergone hysterectomy, the estetrol component is preferably administered as sole active ingredient.

When the present therapy is administered to a patient who still has a uterus, the estetrol component may be administered as sole active ingredient or may be administered together with an optional progestogenic component. Said optional progestogenic component may be administered continuously (i.e. every day in addition to the estetrol component) or sequentially (wherein sequentially means an administration of the progestogenic component during, for example, 10 to 14 days each month or during 14 days every 3 months).

The terms "continuous"/"continuously" as used herein, means that the components are administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be continuous if the longest interval between 2 subsequent administrations is not more than 3.5 times as long as the average interval. Even more preferably said longest interval is not more than 2.5 times, most preferably not more than 1.5 times as long as the average interval.

In one embodiment, the optional progestogenic component is administered via a non-oral route, for example using an Intra Uterine Device (IUD). In one embodiment said IUD delivers the progestogenic component levonorgestrel. In one such embodiment, the IUD is the Mirena® IUD or the Levosert® IUD.

In one embodiment, the present therapy employs oral, sublingual, buccal, or sublabial administration of the estetrol component. These latter 3 modes of administration offer the advantages that the estetrol component does not have to pass through the digestive system and avoids first-pass liver exposure. Furthermore, these modes of administration provide a rapid onset of action.

The term "sublingual" as used herein refers to the pharmacological route of administration by which the estetrol component diffuses into the blood through tissues under the tongue.

The term "buccal" as used herein refers to the pharmacological route of administration by which the estetrol component diffuses into the blood through tissues of the buccal vestibule, the area inside the mouth between the lining of cheek (the buccal mucosa) and the teeth/gums.

The term "sublabial" as used herein refers to the pharmacological route of administration by which the estetrol component is placed between the lip and the gingiva.

In the present method, the estetrol and progestogenic components may be administered in separate dosage units. However, it is also possible and indeed very convenient to combine these two components into a single dosage unit.

In the method according to the present invention the combination of the progestogenic and estetrol component is suitably administered continuously during a period of at least 10 days.

The invention may suitably be reduced to practice in the form of a variety of administration methods that are known to the person skilled in the art. Amongst these methods are the methods making use of monophasic preparations, which contain dosage units with a constant amount of the estetrol component and of the optional progestogenic component.

In the embodiment of the invention where sequential administration of the progestogenic component is chosen, it is also possible and convenient to combine the components into a single dosage unit for the days when the two components are administered.

In one embodiment of the invention, the hormone replacement therapy is administered to a perimenopausal subject. In this embodiment, the subject will benefit from the alleviation of VMS through the administration of the composition of the invention, while simultaneously benefiting from a contraceptive effect. In the specific perimenopausal population, contraception is indeed often required, and since VMS appear during this time of life, the treatment of the invention will uniquely address these two needs in a single and simple treatment. In a particular embodiment of the invention, a hormonal replacement therapy for perimenopausal subjects consists in administering daily amounts of about 15 mg estetrol together with daily amounts of about 3 mg drospirenone, according to a 24/4 administration regimen. As used herein, a "24/4 administration regimen" is a combined monophasic administration regimen which involves the daily administration of the active pharmaceutical ingredients for about 24 days followed by an administration-free interval of about 4 days.

In another embodiment of the invention, the hormone replacement therapy is administered to a postmenopausal subject.

In a particular embodiment of the invention, the hormone replacement therapy is beneficially administered to take advantage of the absence of effect of the smoking status of the subject on the therapy of the invention. It has indeed long been known that smoking significantly reduces serum estrogen concentrations, such as reported for example in the clinical study analysis of Bjarnason et al. (Bjarnason et al.; *Climacteric* 2012; *Acute and long-term estradiol kinetics in smoking postmenopausal women;* 15:5; p. 449-454) who found that in the estrogen group, smoking leads to significantly lower levels of both serum estrone and serum estradiol at all post-randomization time points, while no differences between smokers and non-smokers were seen on placebo. Bjarnason et al. conclude that smoking reduces serum estrogens at both trough and after 2 h in postmenopausal women on estrogen treatment, that the effect of smoking on estrogen concentrations is fully expressed in women smoking ten or less cigarettes daily, and that the influence of smoking upon the metabolism of estrogen therapy is constant and without dose-response for standard smoking intensities.

In this particular embodiment, based on the surprising finding that the therapy of the invention is not affected by the smoking status of the subject, the hormone replacement therapy is preferably administered to a patient population smoking 5 or more cigarettes daily, to a patient population smoking 10 or more cigarettes daily, or to a patient population smoking 15 or more cigarettes daily.

In yet another particular embodiment of the invention, the hormone replacement therapy is beneficially administered to take advantage of the absence of effect of the BMI of the subject on the therapy of the invention. It has indeed been surprisingly found that contrary to the prior art hormone replacement therapies, the efficacy of the therapy of the invention is not affected by the BMI value of the subject. In this particular embodiment, the hormone therapy of the invention is preferably administered to a subject whose BMI is 25 or more, 28 or more, 30 or more, 33 or more, 35 or more, 37 or more, or 40 or more, In this particular embodiment, the hormone therapy of the invention is preferably administered to an overweight subject, or to an obese subject.

The hormone replacement therapy of the invention was found to be particularly beneficial for alleviating menopause-associated symptoms while having an extremely limited impact on a large number of hepatic, haemostatic, endocrine and metabolic parameters. It is indeed the case that the HRT treatments of the prior art have a negative impact on these parameters. Surprisingly and very beneficially, the treatment of the present invention was found by contrast to not modify, or to only minimally modify, most parameters.

Compositions

The estetrol component of the present invention encompasses substances selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. More preferably, the estetrol component is estetrol (including estetrol hydrates). Most preferably, the estetrol component contained in the dosage unit is estetrol monohydrate.

The estetrol component of the invention is used at a daily dose equivalent to about 15 mg of estetrol monohydrate. In other words, when the estetrol component is not estetrol monohydrate itself, the daily dose of the estetrol component is adjusted to yield a therapeutic effect equivalent to that of a daily dose of 15 mg of estetrol monohydrate.

In a particularly preferred embodiment of the invention the pharmaceutical composition according to invention is designed for daily administration, i.e. it represents a daily dosage unit.

In the case of oral administration, the oral dosage unit according to the invention is preferably a solid or semi-solid dosage form such as tablets, capsules, cachets, pellets, pills, powders and granules. The term "solid or semi-solid dosage form" also encompasses capsules that contain a liquid, e.g. an oil, in which the present estetrol component and/or the optional progestogenic component is dissolved or dispersed. Tablets and equivalent solid and semi-solid dosage forms can suitably contain materials such as binders (e.g. hydroxypropylmethyl cellulose, polyvinyl pyrrolidone, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc). These tablets and equivalent solid dosage forms may be prepared by wet granulation, e.g. using an aqueous solution or an organic solution, as well as by direct compression.

In the case of sublingual, buccal or sublabial administration, the pharmaceutical composition according to the invention is preferably an orodispersible dosage unit.

The term "orodispersible dosage unit" as used herein refers to a dosage unit that is designed to rapidly disintegrate in the oral cavity when it comes into contact with saliva and to disperse the estetrol component into the saliva so it may be absorbed through the mucosal lining of the oral cavity.

When the dosage unit is an orodispersible dosage unit, the rate of release of the estetrol component from the dosage unit can suitably be determined using the disintegration test according to Ph. Eur. 2.9.1 ("Disintegration of tablets and capsules") and USP <701> ("Disintegration"), for example using water as the disintegration medium. An orodispersible solid dosage unit of the present invention, when subjected to the aforementioned disintegration test, typically disintegrates within less than 5 minutes, more preferably within less than 2 minutes, still more preferably within less than 1.5 minutes, still more preferably within less than 1 minute, still more preferably within less than 45 seconds, and most preferably within less than 30 seconds.

When the patient still has a uterus, an optional progestogenic component may be administered in addition to the estetrol component.

Examples of progestogenic components which may suitably be used in accordance with the present invention include: levonorgestrel, norgestimate, norethisterone, dydrogesterone, drospirenone, 3-beta-hydroxydesogestrel, 3-ketodesogestrel, 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol, mecirogestone, medroxyprogesterone, megestrol, mele, gestrol, nomegestrol, norethindrone, norethynodrel, norgestrel (including d-norgestrel, and dl-norgestrel), norgestrienone, normethisterone, progesterone, quingestanol, (17 alpha)-17-hydroxy-11-methylene-19-norpregna-4, 15-dien-20-yn-3-one, tibolone, trimegestone, algestone-acetophenide, nestorone, promegestone, 17-hydroxyprogesterone esters, 19-nor-17hydroxyprogesterone, 17alpha-ethynyltestosterone, 17alpha-ethynil-19-nortestosterone, d-17beta-acetoxy-13beta-ethyl-17alpha-ethynylgon-4-en-3-one oxime, 6beta, 7beta; 15beta,16beta-dimethylene-3-oxo-17-pregna-4,9 (11)-diene-21, 17beta-carbolactone or tanaproget and precursors of these compounds that are capable of liberating these progestogens in vivo when used in the present method.

Preferably the progestogenic component used in the present method is selected from the group consisting of progesterone, drospirenone, dydrogesterone, precursors of these progestogens and mixtures thereof.

In one embodiment, the invention provides a combination composition comprising an estetrol component together with progesterone.

In one embodiment, the invention provides a combination composition comprising an estetrol component together with drospirenone.

In one embodiment, the invention provides a combination composition comprising an estetrol component together with dydrogesterone.

When the progestogenic component of the invention is drospirenone, it is preferably used at a daily dose of from 0.5 mg to 10 mg, even more preferably of from 1 mg to 4 mg.

When the progestogenic component of the invention is dydrogesterone, it is preferably used at a daily dose of about 5 mg to about 10 mg, more preferably at a daily dose of about 5 mg.

When the progestogenic component of the invention is progesterone, it is preferably used at a daily dose of from 50 mg to 200 mg. In one embodiment, progesterone is used at a daily dose of 50 mg to 100 mg when it is used continuously. In another embodiment, progesterone is used at a daily dose of 100 mg to 200 mg when it is used sequentially, for example when it is administered during about 14 days every month.

When a different progestogenic component is used, the daily dose is adjusted such as to give the same pharmacological effect as a dose of 50 mg to 200 mg of progesterone.

In a preferred embodiment of the invention, the composition combines the estetrol component and the optional progestogenic component into a single dosage unit, preferably a daily dosage unit. In a more preferred embodiment of the invention, said combined daily dosage unit is an oral combined daily dosage unit.

In one embodiment, the invention provides an oral combined daily dosage unit comprising an estetrol component and progesterone.

In one embodiment, the invention provides an oral combined daily dosage unit comprising an estetrol component and drospirenone.

In one embodiment, the invention provides an oral combined daily dosage unit comprising an estetrol component and dydrogesterone.

In a particular embodiment of the invention wherein the treated subjects are perimenopausal subjects, the compositions of the invention are supplied as a kit-of-parts, wherein in a suitable packaging such as a blister pack, individual daily dosage units for an administration period of about 28 days are supplied. Preferably said daily dosage units are oral daily dosage units.

In a preferred embodiment for the treatment of perimenopausal subjects, a kit of parts containing 24 daily dosage units comprising estetrol and drospirenone in addition to 4 placebo daily dosage units is provided. In yet a preferred embodiment for the treatment of perimenopausal subjects, the kit of parts contains 24 daily dosage units each comprising about 15 mg of estetrol and about 3 mg of drospirenone, in addition to 4 placebo daily dosage units.

In a preferred embodiment of the invention, the composition combines estetrol at a daily dose of about 15 mg with progesterone at a daily dose of about 100 mg.

In another embodiment of the invention, the estetrol component is administered to a patient who still has a uterus in conjunction with a Selective Estrogen Receptor Modulator (SERM), in particular in conjunction with bazedoxifene. Preferably bazedoxifene is administered at a daily dose of about 10 mg to 50 mg. More preferably, bazedoxifene is administered at a daily dose of about 20 mg.

In one embodiment, the invention provides a combination therapy comprising an estetrol component together with bazedoxifene.

In one embodiment, the invention provides an oral combined daily dosage unit comprising an estetrol component and bazedoxifene.

The present invention has been described above with reference to a number of exemplary embodiments. Modifications and alternative implementations of some parts or elements are possible, and are included in the scope of protection as defined in the appended claims.

EXAMPLES

Example 1—A Dose-Finding Study to Select the Daily Oral Dose of Estetrol (E4) for the Treatment of Vasomotor Symptoms in Post-Menopausal Women Study Enrolment and Duration:
Enrolment was approximately 18 months. Individual subject participation was up to 27 weeks: up to 6 weeks pre-screening and washout, up to 4 weeks screening and run-in period, up to 91 days (13 weeks) of E4/placebo treatment followed by 2 weeks (14 days) of progestin therapy and a Follow up visit 1 week after completion of progestin therapy in non-hysterectomised subjects only.
Primary Efficacy Objective:
To define the minimum effective dose (MED) of the oral dose of E4 by evaluating changes in frequency and in severity of moderate to severe vasomotor symptoms (VMS).
Methodology:
This was a prospective, multicentre, randomised, placebo-controlled, double-blinded, dose-finding study.
Subject Population:
Eligible subjects were hysterectomised and non-hysterectomised post-menopausal women aged 40 to 65 years, inclusive, presenting at least 7 moderate to severe hot flushes/day or at least 50 moderate to severe hot flushes/week.
Diagnosis and Inclusion Criteria:
The subjects have met all of the following inclusion criteria at the randomization visit. These criteria were assessed during the screening period:
1. Women aged 40 to 65 years, inclusive, presenting at least 7 moderate to severe hot flushes/day or at least 50 moderate to severe hot flushes/week in the week preceding randomization.
2. Body Mass Index (BMI) between 18.0 and 35.0 kg/m$^2$, inclusive.
3. Post-menopausal status defined as levels of follicle stimulating hormone (FSH) >40 IU/L and:
   amenorrhoea for at least 12 consecutive months or,
   amenorrhoea for at least 6 months with estradiol (E2)<20 pg/mL or,
   at least 6 weeks post-surgical bilateral oophorectomy with or without hysterectomy with a copy of the pathology report or a statement on letterhead from the subject's physician documenting both ovaries were removed is required.
4. For non-hysterectomised women: intact uterus with bi-layer endometrial thickness mm on TVUS.
5. Negative pregnancy test.
6. Good physical and mental health, in the judgement of the Principal Investigator (PI), on the basis of medical, surgical and gynaecological history, physical examination, gynaecological examination, clinical laboratory, and vital signs.
7. Subject has provided signed and dated written informed consent before admission to the study.
8. Subject is able to understand and comply with the protocol requirements, instructions, and protocol-stated restrictions.

Exclusion Criteria:
Potential study subjects were excluded if one of the following exclusion criteria was present at the randomization visit. These criteria were assessed during the screening period:
1. For non-hysterectomised women: uterine disease or medical condition including:
   a. Bi-layer endometrial thickness >5 mm as determined by TVUS;
   b. Presence of fibroid(s) that obscure(s) evaluation of endometrium by TVUS;
   c. History or presence of uterine cancer;
   d. Presence of endometrial hyperplasia;
   e. Presence of an endometrial polyp with hyperplastic or malignant epithelium.
2. Undiagnosed vaginal bleeding in the last 12 months.
3. Any history of malignancy with the exception of basal cell (excluded if within the prior 2 years) or squamous cell (excluded if within the prior one year) carcinoma of the skin. Any clinically significant findings at the breast examination and/or on mammography suspicious of breast malignancy that would require additional clinical testing to rule out breast cancer (however, simple cysts confirmed by ultrasound were allowed). Note: A screening mammogram was required unless the subject had a written documentation of a mammogram performed within the last 9 months.
4. Abnormal cervical Pap smear in non-hysterectomised subjects (written documentation of prior test within 18 months or test at screening exam) with evidence of cervical dysplasia greater than low grade squamous intraepithelial lesion (LSIL). Women with a diagnosis of atypical squamous cells of undetermined significance (ASCUS) were enrolled.
5. Systolic blood pressure (BP) outside the range 90 to 140 mmHg, diastolic BP outside the range 60 to 90 mmHg, and/or heart rate outside the range 40 to 100 bpm. Subjects with mild to moderate hypertension who were controlled on a stable antihypertension regimen were enrolled if they met the inclusion/exclusion criteria.
6. Any clinically significant abnormality identified on the screening 12-lead ECG.
7. History of venous or arterial thromboembolic disease (e.g., deep vein thrombosis, pulmonary embolism, stroke, myocardial infarction, angina pectoris, etc.), history of known coagulopathy or abnormal coagulation factors.
8. Diabetes mellitus with poor glycaemic control in the last 6 months assessed by laboratory values of glucose outside the normal ranges and glycated haemoglobin above 7%.
9. Dyslipoproteinaemia predisposes the subject to atherosclerotic cardiovascular disease (ASCVD).
   If a subject had a 10 years ASCVD score ≥5% as calculated using the ASCVD risk estimator (ACC/AHA Cardiovascular risk assessment guideline, 2013), she was not be included in the trial. In all cases, LDL cholesterol level ≥190 mg/dL or triglycerides plasma level >400 mg/dL were exclusionary.
   If a subject was receiving a lipid-lowering therapy, her treatment had to be on a stable dose for at least 1 month before screening and the same eligibility criteria had to be used.
10. Smoking >10 cigarettes/day or use of >1 ml/day of nicotine containing liquid for electronic cigarette.
11. Presence or history of gallbladder disease, unless cholecystectomy had been performed.
12. Systemic lupus erythematosus.
13. Multiple sclerosis.
14. Acute or chronic liver disease.
15. Acute or chronic renal impairment, including severe renal impairment.
16. Uncontrolled thyroid disorders.
17. Subject had a history of major depression or post-traumatic stress disorder (PTSD) within 2 years, OR a history of other major psychiatric disorder at any time (e.g., schizophrenia, bipolar disorder, etc.).
18. Use of oestrogen or progestin containing drug(s). A washout period is required before the Run-in Period in case of use of:
   a. Vaginal hormonal products (rings, creams, gels): washout of at least 4 weeks;
   b. Transdermal oestrogen or oestrogen/progestin: washout of at least 4 weeks;
   c. Oral oestrogen and/or progestin: washout of at least 4 weeks;
   d. Intrauterine progestin therapy: washout of at least 4 weeks;
   Current users of progestin implants or oestrogen alone injectable drug therapy were not allowed to participate unless the treatment was stopped more than 3 months ago. Current users of oestrogen pellet therapy or progestin injectable drug therapy were not allowed to participate unless the treatment was stopped more than 6 months ago.
19. Use of non-hormonal treatments to reduce hot flushes. A washout period of 1 week was required before the Run-in Period in the case of use of non-hormonal prescription and over-the-counter (OTC) treatments for hot flushes (such as anti-depressants paroxetine, escitalopram, venlafaxine, desvenlafaxine, and clonidine; or phytoestrogens, black cohosh, etc.). If one of these treatments was concomitantly taken with an oestrogen or progestin-containing drug, washout periods could be combined and did not have to be sequential.
20. Use of medication that may affect the outcome of the VMS endpoints within 28 days before the Run-in Period. This included (but was not limited to): SSRIs [selective serotonin reuptake inhibitors], SNRIs [serotonin and norepinephrine reuptake inhibitors], dopaminergic or antidopaminergic drugs, or gabapentin.
21. History or presence of allergy to the investigational product or drugs of this class, or history of drug or other allergy that, in the opinion of the Investigator contraindicated subject participation.
22. History or presence of allergy or intolerance to any component of the investigational product.
23. History of alcohol or substance abuse or dependence in the 12 months as determined by the Investigator, i.e. subject consumed excessive alcohol, abused drugs, or had a condition that could compromise the subject's ability to comply with study requirements in the Investigator's opinion.
24. Sponsor or Contract Research Organization (CRO) employees, or personnel in the department of the Investigator and relatives affiliated with this study.
25. Subjects with *porphyria* and subjects with known or suspected history of a clinically significant systemic disease, unstable medical disorders, life-threatening disease or current malignancies that would pose a risk to the subject in the opinion of the Investigator.
26. Participation in another investigational drug clinical study within 1 month (30 days) or had received an investigational drug within the last 3 months (90 days).
27. Was judged by the Investigator to be unsuitable for any reason.

Number of Subjects:
Intention-to-Treat Principle

This principle asserts that the effect of a treatment policy can be best assessed by evaluating on the basis of the intention to treat a subject (i.e. the planned treatment regimen) rather than the actual treatment given. It has the consequence that subjects allocated to a treatment group should be followed up, assessed and analysed as members of that group irrespective of their compliance to the planned course of treatment.

Further, the intention-to-treat principle implies that the primary analysis should include all randomised subjects.

Preservation of the initial randomisation in analysis is important in preventing bias and in providing a secure foundation for statistical tests. In many clinical trials the use of the full analysis set provides a conservative strategy. Under many circumstances it may also provide estimates of treatment effects which are more likely to mirror those observed in subsequent practice.

In the present study, the Intention-To-Treat group included a total of 257 patients. Subjects were randomly allocated to one of the 5 treatment arms in a 1:1:1:1:1 ratio. The randomisation was stratified by centre.

Study Visits:

| Week | Visit | Notation as used throughout all tables, listings and figures | Study part |
|---|---|---|---|
| Week −7 to −4 | Visit 1 (Pre-Screening) | V1 | Screening |
| Week −4 to −3 | Visit 1a (Screening) | V1a | Screening |
| Week −1 | Visit 2 (Baseline) | V2 | Randomisation |
| Week 5 | Visit 3 | V3 | Treatment period |
| Week 13 | Visit 4 (EOT) | V4 | End of treatment |
| Week 16 | Visit 5 (EOS) | V5 | End of study |

Test Product and Reference Therapy, Dose, and Mode of Administration

All treatments (Estetrol, hereinafter, E4, [2.5 mg, 5 mg, 10 mg, 15 mg] capsule) were administered once daily (QD) per os for at least 12 consecutive weeks until the last biological assessments (Day 91 maximum) had been performed.

Placebo, 1 capsule administered QD per os for at least 12 consecutive weeks until the last biological assessments (Day 90 maximum) have been performed.

If during the course of the trial, a double layer endometrial thickness ≥15 mm was detected on TVUS and/or abnormal uterine bleeding (in the judgement of the gynecologist in light of the oestrogen therapy) was reported by a non-hysterectomised woman, she underwent an endometrial biopsy and was treated with progestin (10 mg dydrogesterone) QD until end of Week 11 in a sequential way (i.e., a 14 day progestin treatment period followed by a 14 day progestin treatment pause) in addition to the E4/placebo treatment. If the endometrial biopsy showed endometrial hyperplasia, the subject participation was immediately stopped and the treatment of hyperplasia was performed as per local guidelines. If an abnormal uterine bleeding occurred again after a first normal endometrial biopsy, a thorough gynaecological examination and a TVUS were performed. If necessary in the judgment of the gynecologist, a second endometrial biopsy was performed. After the E4/Placebo treatment period, all non-hysterectomised subjects (including those having received the progestin previously) received progestin therapy for 14 days with 10 mg dydrogesterone QD.

Results

A. Vasomotors Parameters for Each of the 5 Treatment Groups a. VMS frequency
  i. Absolute change (mean change from baseline) in weekly frequency of moderate to severe VMS
     a) Week-by-week for each group

| | 2.5 mg | | 5 mg | | 10 mg | | 15 mg | | Placebo | |
|---|---|---|---|---|---|---|---|---|---|---|
| Week | Mean | SD | Mean | SD | Mean | SD | Mean | SD | Mean | SD |
| 0 | 0.00 | 0.00 | 0.00 | 0.00 | 0.00 | 0.00 | 0.00 | 0.00 | 0.00 | 0.00 |
| 1 | −17.28 | 19.71 | −15.04 | 17.36 | −13.37 | 19.59 | −14.86 | 16.45 | −16.65 | 16.24 |
| 2 | −25.10 | 23.91 | −21.68 | 19.26 | −23.47 | 24.74 | −29.19 | 20.25 | −27.38 | 23.16 |
| 3 | −32.46 | 26.15 | −24.38 | 21.36 | −31.34 | 25.21 | −36.30 | 23.23 | −30.16 | 23.09 |
| 4 | −35.89 | 31.57 | −27.57 | 22.47 | −36.38 | 22.62 | −41.43 | 21.60 | −32.94 | 23.14 |
| 5 | −37.16 | 33.27 | −30.70 | 23.05 | −39.07 | 21.55 | −44.34 | 20.95 | −34.70 | 23.01 |
| 6 | −39.98 | 35.44 | −38.02 | 22.13 | −42.56 | 21.18 | −46.58 | 19.83 | −37.18 | 21.25 |
| 7 | −42.44 | 36.96 | −38.23 | 21.73 | −43.30 | 22.18 | −48.51 | 19.34 | −38.55 | 21.85 |
| 8 | −43.62 | 38.43 | −38.55 | 23.54 | −44.46 | 23.30 | −48.35 | 19.75 | −38.13 | 21.69 |
| 9 | −45.19 | 36.91 | −39.34 | 23.51 | −45.19 | 24.22 | −49.62 | 18.97 | −39.25 | 22.74 |
| 10 | −45.54 | 37.93 | −39.83 | 23.79 | −45.93 | 23.58 | −48.88 | 20.04 | −41.12 | 21.82 |
| 11 | −44.74 | 39.30 | −41.46 | 23.59 | −45.90 | 23.57 | −49.92 | 19.42 | −42.50 | 22.68 |
| 12 | −45.04 | 38.91 | −40.60 | 24.37 | −47.21 | 22.87 | −50.94 | 18.38 | −42.97 | 22.31 |

In order to analyse the data recorded in this study, treatment groups have been compared using an ANCOVA (analysis of covariance) with respect to the change in weekly frequency of moderate to severe VMS from baseline to weeks 4 and 12. The ANCOVA model includes treatment ("trt1") and study centre ("SITEPOOL") as a fixed effect and baseline ("base") as a covariate.

b) Covariate Significance

The Table below presents a comparison over all treatment groups.

| Analysis Timepoint (N) | Covariate | p_value |
|---|---|---|
| 4 | trt1 | 0.0164 |
| 4 | base | <.0001 |
| 4 | SITEPOOL | 0.2214 |
| 12 | trt1 | 0.0384 |
| 12 | base | <.0001 |
| 12 | SITEPOOL | 0.2706 |

Upon review, it was considered that the effect due to the study centre was not very important, and a second ANCOVA was performed without accounting for study centres.

Without Site Effect

| Analysis Timepoint (N) | Covariate | p_value |
|---|---|---|
| 4 | trt1 | 0.0130 |
| 4 | base | <.0001 |
| 12 | trt1 | 0.0254 |
| 12 | base | <.0001 | c) The Table below presents mean change from baseline by week and treatment:

| Analysis Timepoint (N) | Planned treatment (mg) | LS adjusted mean | Lower 95% confidence limit | Upper 95% confidence limit |
|---|---|---|---|---|
| 4 | 0 | −33.7959277 | −40.006133 | −27.585722 |
| 4 | 2.5 | −32.2601479 | −38.742792 | −25.777504 |
| 4 | 5 | −27.4372730 | −34.135693 | −20.738853 |
| 4 | 10 | −35.3672857 | −41.716169 | −29.018402 |
| 4 | 15 | −43.5996056 | −50.256441 | −36.942770 |
| 12 | 0 | −43.7344395 | −50.150527 | −37.318352 |
| 12 | 2.5 | −40.1310220 | −46.828579 | −33.433465 |
| 12 | 5 | −40.6802008 | −47.600688 | −33.759714 |
| 12 | 10 | −45.8376026 | −52.396965 | −39.278240 |
| 12 | 15 | −53.8273074 | −60.704831 | −46.949784 |

Without Site Effect

| Analysis Timepoint (N) | Planned treatment (mg) | LS adjusted mean | Lower 95% confidence limit | Upper 95% confidence limit |
|---|---|---|---|---|
| 4 | 0 | −33.6519764 | −39.821576 | −27.482377 |
| 4 | 2.5 | −32.6798943 | −39.056255 | −26.303533 |
| 4 | 5 | −27.8705668 | −34.540176 | −21.200958 |
| 4 | 10 | −35.8741722 | −42.156516 | −29.591828 |
| 4 | 15 | −44.3569892 | −50.965323 | −37.748656 |
| 12 | 0 | −43.9304437 | −50.292513 | −37.568374 |
| 12 | 2.5 | −40.6840423 | −47.259323 | −34.108761 |
| 12 | 5 | −41.0122585 | −47.889936 | −34.134581 |
| 12 | 10 | −46.5333871 | −53.011718 | −40.055056 |
| 12 | 15 | −54.9073270 | −61.721817 | −48.092837 |

All statistical tests are supported by presenting Least Square adjusted mean (LS adjusted mean: the group means after having controlled for a covariate; also referred to as marginal means or estimated marginal means) and 95% confidence intervals for the respective treatment effects.

These LS adjusted means and Confidence Intervals are based on the statistical models used for the analysis.

The Confidence Intervals implies that if the same population is sampled on numerous occasions and interval estimates are made on each occasion, the resulting intervals would bracket the true population parameter in approximately 95% of the cases.

d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | 1.535780 | −9.602669 | 12.674228 | 0.99183 |
| 4 | 5.0 | 0 | 6.358655 | −4.958071 | 17.675380 | 0.44910 |
| 4 | 10.0 | 0 | −1.571358 | −12.573355 | 9.430639 | 0.99067 |
| 4 | 15.0 | 0 | −9.803678 | −21.033229 | 1.425873 | 0.10653 |
| 12 | 2.5 | 0 | 3.603418 | −7.904295 | 15.111130 | 0.86103 |
| 12 | 5.0 | 0 | 3.054239 | −8.637660 | 14.746138 | 0.92091 |
| 12 | 10.0 | 0 | −2.103163 | −13.469900 | 9.263574 | 0.97581 |
| 12 | 15.0 | 0 | −10.092868 | −21.694703 | 1.508967 | 0.10838 |

Without Site Effect

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | 0.972082 | −10.164048 | 12.108212 | 0.99860 |
| 4 | 5.0 | 0 | 5.781410 | −5.579628 | 17.142447 | 0.53888 |
| 4 | 10.0 | 0 | −2.222196 | −13.242056 | 8.797664 | 0.96728 |
| 4 | 15.0 | 0 | −10.705013 | −21.979289 | 0.569264 | 0.06834 |
| 12 | 2.5 | 0 | 3.246401 | −8.237137 | 14.729940 | 0.89864 |
| 12 | 5.0 | 0 | 2.918185 | −8.797276 | 14.633647 | 0.93259 |
| 12 | 10.0 | 0 | −2.602943 | −13.966584 | 8.760697 | 0.94911 |
| 12 | 15.0 | 0 | −10.976883 | −22.602878 | 0.649111 | 0.07057 |

From these Tables, it can be seen that the 15 mg daily dose generates a near statistically significant difference with placebo at 4 weeks (p-value of 0.10653 in the first statistical analysis, and of 0.06834 in the analysis without pooled site) and at 12 weeks (p-value of 0.10838 in the first statistical analysis, and of 0.07057 in the analysis without pooled site).

ii. Relative change (% from baseline) in weekly frequency of moderate to severe VMS
a) Week-by-week for each group

|      | 2.5 mg | | 5 mg | | 10 mg | | 15 mg | | Placebo | |
|------|--------|-----|------|-----|-------|-----|-------|-----|---------|-----|
| Week | Mean | SD | Mean | SD | Mean | SD | Mean | SD | Mean | SD |
| 0 | 0% | 0% | 0% | 0% | 0% | 0% | 0% | 0% | 0% | 0% |
| 1 | −23% | 23% | −23% | 28% | −21% | 29% | −22% | 33% | −26% | 25% |
| 2 | −34% | 27% | −33% | 29% | −37% | 37% | −46% | 34% | −41% | 35% |
| 3 | −44% | 29% | −38% | 33% | −48% | 39% | −57% | 34% | −45% | 33% |
| 4 | −49% | 33% | −43% | 34% | −55% | 35% | −67% | 30% | −49% | 32% |
| 5 | −50% | 33% | −47% | 34% | −60% | 33% | −72% | 28% | −52% | 32% |
| 6 | −54% | 36% | −57% | 31% | −65% | 33% | −76% | 26% | −56% | 30% |
| 7 | −57% | 36% | −57% | 30% | −66% | 34% | −79% | 25% | −58% | 30% |
| 8 | −58% | 38% | −57% | 32% | −68% | 35% | −79% | 26% | −58% | 31% |
| 9 | −61% | 36% | −59% | 32% | −69% | 36% | −81% | 24% | −60% | 31% |
| 10 | −61% | 37% | −60% | 32% | −70% | 35% | −80% | 27% | −63% | 30% |
| 11 | −60% | 39% | −63% | 31% | −70% | 34% | −82% | 25% | −65% | 31% |
| 12 | −61% | 38% | −62% | 32% | −72% | 33% | −84% | 23% | −65% | 30% |

From this table, it can be seen that the 15 mg daily dose resulted in a reduction of over 80% in the frequency of moderate to severe VMS when compared to baseline.

b) Covariate significance

The Table below presents a comparison over all treatment groups.

| Analysis Timepoint (N) | Covariate | p_value |
|---|---|---|
| 4 | trt1 | 0.0147 |
| 4 | base | 0.3684 |
| 4 | SITEPOOL | 0.3236 |
| 12 | trt1 | 0.0100 |
| 12 | base | 0.1490 |
| 12 | SITEPOOL | 0.0958 |

Without Site Effect

| Analysis Timepoint (N) | Covariate | p_value |
|---|---|---|
| 4 | trt1 | 0.0107 |
| 4 | base | 0.2264 |
| 12 | trt1 | 0.0065 |
| 12 | base | 0.0774 | c) The Table below presents mean relative change (%) from baseline by week and treatment

| Analysis Timepoint (N) | Planned treatment (mg) | LS adjusted mean | Lower 95% confidence limit | Upper 95% confidence limit |
|---|---|---|---|---|
| 4 | 0 | −0.49080693 | −0.578953 | −0.402661 |
| 4 | 2.5 | −0.48482309 | −0.576836 | −0.392811 |
| 4 | 5 | −0.42247695 | −0.517552 | −0.327402 |
| 4 | 10 | −0.54456428 | −0.634678 | −0.454450 |
| 4 | 15 | −0.64721795 | −0.741703 | −0.552733 |
| 12 | 0 | −0.64237949 | −0.726371 | −0.558388 |
| 12 | 2.5 | −0.60565210 | −0.693328 | −0.517976 |
| 12 | 5 | −0.60259514 | −0.693189 | −0.512001 |
| 12 | 10 | −0.70041629 | −0.786283 | −0.614549 |
| 12 | 15 | −0.80089486 | −0.890927 | −0.710863 |

Without Site Effect

| Analysis Timepoint (N) | Planned treatment (mg) | LS adjusted mean | Lower 95% confidence limit | Upper 95% confidence limit |
|---|---|---|---|---|
| 4 | 0 | −0.48986685 | −0.577115 | −0.402619 |
| 4 | 2.5 | −0.49532213 | −0.585494 | −0.405151 |
| 4 | 5 | −0.43132298 | −0.525642 | −0.337004 |
| 4 | 10 | −0.55503454 | −0.643877 | −0.466192 |
| 4 | 15 | −0.66014529 | −0.753597 | −0.566693 |
| 12 | 0 | −0.65107969 | −0.735113 | −0.567046 |
| 12 | 2.5 | −0.62210640 | −0.708956 | −0.535256 |
| 12 | 5 | −0.61436957 | −0.705214 | −0.523525 |
| 12 | 10 | −0.71732171 | −0.802891 | −0.631752 |
| 12 | 15 | −0.82338275 | −0.913392 | −0.733373 | d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | 0.005984 | −0.152112 | 0.164079 | 0.99995 |
| 4 | 5.0 | 0 | 0.068330 | −0.092296 | 0.228956 | 0.68478 |
| 4 | 10.0 | 0 | −0.053757 | −0.209916 | 0.102401 | 0.81738 |
| 4 | 15.0 | 0 | −0.156411 | −0.315800 | 0.002977 | 0.05622 |
| 12 | 2.5 | 0 | 0.036727 | −0.113917 | 0.187372 | 0.93696 |
| 12 | 5.0 | 0 | 0.039784 | −0.113271 | 0.192840 | 0.92218 |
| 12 | 10.0 | 0 | −0.058037 | −0.206836 | 0.090762 | 0.74506 |
| 12 | 15.0 | 0 | −0.158515 | −0.310392 | −0.006639 | 0.03771 |

From this Table it can be seen that the 15 mg daily dose generates a statistically significant difference with placebo at 12 weeks (p-value of 0.03771) and an almost statistically significant difference with placebo at 4 weeks (p-value of 0.05622).

It is particularly striking to observe the low p-values obtained for the 15 mg dose by comparison to the elevated p-values obtained for the 10 mg dose.

Without Site Effect

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | −0.005455 | −0.162937 | 0.152027 | 0.99996 |
| 4 | 5.0 | 0 | 0.058544 | −0.102119 | 0.219206 | 0.78717 |
| 4 | 10.0 | 0 | −0.065168 | −0.221006 | 0.090670 | 0.69797 |
| 4 | 15.0 | 0 | −0.170278 | −0.329714 | −0.010843 | 0.03206 |
| 12 | 2.5 | 0 | 0.028973 | −0.122708 | 0.180654 | 0.97301 |
| 12 | 5.0 | 0 | 0.036710 | −0.118034 | 0.191454 | 0.94271 |
| 12 | 10.0 | 0 | −0.066242 | −0.216339 | 0.083855 | 0.65761 |
| 12 | 15.0 | 0 | −0.172303 | −0.325866 | −0.018741 | 0.02210 |

From this Table it can be seen that in the statistical analysis not accounting for site effects, the 15 mg daily dose generates a statistically significant difference with placebo at 4 weeks (p=0.03206) and at 12 weeks (p=0.02210).

It is particularly striking to observe the low p-values obtained for the 15 mg dose by comparison to the elevated p-values obtained for the 10 mg dose.

iii. Frequency changes in groups of responders in weekly frequency of moderate to severe VMS VMS frequency was also studied by grouping patients according to their degree of response.

A first grouping of patients showing a response of 50% or more (relative change from baseline) was prepared. According to this analysis, at week 12, the 15 mg daily dose group contains 91.8% of responders, while the placebo group contains 65.5% of responders. The difference between these two groups has a p-value below 0.01, whereas the difference between the 10 mg daily dose group and the placebo group is not statistically significant (p value >0.1).

A second grouping of patients showing a response of 75% or more was prepared. According to this analysis, at week 12, the 15 mg daily dose group contains 77.6% of responders, while the placebo group contains 43.6% of responders. The difference between these two group has a p-value below 0.001, whereas the difference between the 10 mg daily dose group and the placebo group is not statistically significant (p value >0.05).

b. VMS Severity
  i. Absolute change (mean change from baseline) in weekly severity of moderate to severe VMS
    a) Week-by-week for each group

| Week | 2.5 mg Mean | 5 mg Mean | 10 mg Mean | 15 mg Mean | Placebo Mean |
|---|---|---|---|---|---|
| 0 | 0 | 0 | 0 | 0 | 0 |
| 1 | −0.1542 | −0.098 | −0.2028 | −0.072 | −0.1638 |
| 2 | −0.2112 | −0.1199 | −0.3007 | −0.2853 | −0.2746 |
| 3 | −0.3246 | −0.1574 | −0.3983 | −0.4842 | −0.2676 |
| 4 | −0.3373 | −0.2341 | −0.4842 | −0.5897 | −0.3327 |
| 5 | −0.3984 | −0.1683 | −0.5107 | −0.7432 | −0.4146 |
| 6 | −0.5014 | −0.3212 | −0.6086 | −0.7035 | −0.45 |
| 7 | −0.4562 | −0.2787 | −0.643 | −0.8112 | −0.4645 |
| 8 | −0.5359 | −0.3239 | −0.6644 | −0.8854 | −0.52 |
| 9 | −0.5465 | −0.3249 | −0.6864 | −0.9092 | −0.5522 |
| 10 | −0.6052 | −0.3667 | −0.709 | −0.9628 | −0.5514 |
| 11 | −0.5564 | −0.4161 | −0.666 | −1.0123 | −0.6551 |
| 12 | −0.6279 | −0.4007 | −0.6941 | −1.0425 | −0.6604 |

In order to better analyse the data recorded in this study, treatment groups have been compared using an ANCOVA (analysis of covariance) with respect to the change in severity of moderate to severe VMS from baseline to mild, moderate and severe VMS at week 4 and week 12 for each active treatment versus placebo. For women who experienced 100% VMS relief at week 4 and/or week 12, a value of zero was attributed. The ANCOVA model includes treatment ("trt1") as a fixed effect and baseline ("base") as a covariate.

b) Covariate significance

The Table below presents a comparison over all treatment groups.

| Analysis Timepoint (N) | Covariate | p_value |
|---|---|---|
| 4 | trt1 | 0.0119 |
| 4 | base | 0.3781 |
| 12 | trt1 | 0.0032 |
| 12 | base | 0.7990 | c) The Table below presents mean change from baseline by week and treatment:

| Analysis Timepoint (N) | Planned treatment (mg) | LS adjusted mean | Lower 95% confidence limit | Upper 95% confidence limit |
|---|---|---|---|---|
| 4 | 0 | −0.327801 | −0.470747 | −0.184854 |
| 4 | 2.5 | −0.341092 | −0.486518 | −0.195666 |
| 4 | 5 | −0.238552 | −0.393041 | −0.084063 |
| 4 | 10 | −0.482536 | −0.627769 | −0.337303 |
| 4 | 15 | −0.588755 | −0.739764 | −0.437746 |
| 12 | 0 | −0.658280 | −0.868694 | −0.447865 |
| 12 | 2.5 | −0.629592 | −0.843656 | −0.415528 |
| 12 | 5 | −0.402567 | −0.629971 | −0.175163 |
| 12 | 10 | −0.693404 | −0.907183 | −0.479624 |
| 12 | 15 | −1.042087 | −1.264369 | −0.819805 | d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | −0.013291 | −0.268767 | 0.242185 | 0.9998 |
| 4 | 5.0 | 0 | 0.089249 | −0.174507 | 0.353004 | 0.8253 |
| 4 | 10.0 | 0 | −0.154735 | −0.409222 | 0.099751 | 0.3767 |
| 4 | 15.0 | 0 | −0.260954 | −0.520749 | −0.001159 | 0.0486 |
| 12 | 2.5 | 0 | 0.028687 | −0.347368 | 0.404743 | 0.9992 |
| 12 | 5.0 | 0 | 0.255713 | −0.132530 | 0.643955 | 0.3062 |
| 12 | 10.0 | 0 | −0.035124 | −0.409723 | 0.339475 | 0.9981 |
| 12 | 15.0 | 0 | −0.383807 | −0.766221 | −0.001394 | 0.0489 |

From this Table it can be seen that the 15 mg daily dose generates a statistically significant difference with placebo at 4 weeks (p-value of 0.0486) and at 12 weeks (p-value of 0.0489). The 15 mg dose thus significantly improves the severity of VMS at weeks 4 and 12 compared with placebo.

For the severity parameter also, the difference between the 10 mg and 15 mg doses is impressive: this is reflected firstly in the mean changes from baseline presented in the Table of section c) above, where for example at 12 weeks the LS adjusted mean for 10 mg is −0.69 (to be compared with −0.66 found for the placebo group), while it is −1.04 for the 15 mg daily dose group. This clear difference is mirrored by a near 8-fold improvement in the p-value at 4 weeks when switching from 10 mg to 15 mg per day, and an over 20-fold improvement in the p-value at 12 weeks when switching from 10 mg to 15 mg per day.

ii. Relative change (% from baseline) in weekly severity of moderate to severe VMS a) Week-by-week for each group

| Week | 2.5 mg Mean | 5 mg Mean | 10 mg Mean | 15 mg Mean | Placebo Mean |
|---|---|---|---|---|---|
| 0 | 0% | 0% | 0% | 0% | 0% |
| 1 | −7% | −4% | −8% | −3% | −7% |
| 2 | −9% | −5% | −13% | −12% | −12% |
| 3 | −14% | −7% | −17% | −20% | −11% |
| 4 | −15% | −10% | −20% | −24% | −14% |
| 5 | −17% | −7% | −21% | −31% | −18% |
| 6 | −22% | −14% | −26% | −30% | −19% |
| 7 | −20% | −12% | −27% | −34% | −20% |
| 8 | −24% | −14% | −28% | −37% | −22% |
| 9 | −24% | −14% | −28% | −38% | −23% |
| 10 | −26% | −15% | −29% | −40% | −23% |
| 11 | −25% | −18% | −25% | −42% | −28% |
| 12 | −28% | −17% | −28% | −44% | −27% |

From this table, it can be seen that the 15 mg daily dose resulted in a reduction of over 40% in the severity of moderate to severe VMS when compared to baseline.

b) Covariate significance

The Table below presents a comparison over all treatment groups.

| Analysis Timepoint (N) | Covariate | p_value |
|---|---|---|
| 4 | trt1 | 0.0126 |
| 4 | base | 0.6594 |
| 12 | trt1 | 0.0031 |
| 12 | base | 0.1651 | c) The Table below presents mean relative change from baseline by

| Analysis Timepoint (N) | Planned treatment (mg) | LS adjusted mean | Lower 95% confidence limit | Upper 95% confidence limit |
|---|---|---|---|---|
| 4 | 0 | −0.140987 | −0.200215 | −0.081759 |
| 4 | 2.5 | −0.145345 | −0.205600 | −0.085090 |
| 4 | 5 | −0.095556 | −0.159566 | −0.031546 |
| 4 | 10 | −0.201564 | −0.261739 | −0.141388 |
| 4 | 15 | −0.242707 | −0.305276 | −0.180139 |
| 12 | 0 | −0.279744 | −0.368327 | −0.191161 |
| 12 | 2.5 | −0.275038 | −0.365158 | −0.184919 |
| 12 | 5 | −0.164881 | −0.260616 | −0.069145 |
| 12 | 10 | −0.286159 | −0.376158 | −0.196159 |
| 12 | 15 | −0.437476 | −0.531055 | −0.343897 | d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | −0.004358 | −0.110211 | 0.101495 | 0.9999 |
| 4 | 5.0 | 0 | 0.045431 | −0.063853 | 0.154714 | 0.7006 |
| 4 | 10.0 | 0 | −0.060577 | −0.166020 | 0.044866 | 0.4281 |
| 4 | 15.0 | 0 | −0.101720 | −0.209363 | 0.005922 | 0.0702 |
| 12 | 2.5 | 0 | 0.004705 | −0.153612 | 0.163022 | 1.0000 |
| 12 | 5.0 | 0 | 0.114863 | −0.048585 | 0.278310 | 0.2522 |
| 12 | 10.0 | 0 | −0.006415 | −0.164119 | 0.151289 | 0.9999 |
| 12 | 15.0 | 0 | −0.157732 | −0.318726 | 0.003261 | 0.0568 |

From this Table it can be seen that the 15 mg daily dose generates a near statistically significant difference with placebo at 12 weeks (p-value of 0.0568). The 15 mg daily dose improves the severity of VMS at weeks 4 and 12 compared with placebo, whereas the 10 mg daily dose here again is hardly distinguishable from placebo, especially so at 12 weeks.

c. Hot Flush Weekly Weighted Score
  i. Absolute change (mean change from baseline) in weekly weighted score
    a) Week-by-week for each group

| Week | 2.5 mg Mean | 5 mg Mean | 10 mg Mean | 15 mg Mean | Placebo Mean |
|---|---|---|---|---|---|
| 0 | 2.4151 | 1.8297 | 2.3773 | 2.219 | 2.0545 |
| 1 | −40.805 | −33.7092 | −31.4591 | −33.1745 | −38.203 |
| 2 | −58.6163 | −49.1319 | −54.0849 | −67.6983 | −64.1272 |
| 3 | −74.8798 | −56.9697 | −73.5189 | −85.1915 | −70.45 |
| 4 | −82.75 | −64.8344 | −87.2673 | −98.8329 | −77.936 |
| 5 | −84.6062 | −71.6181 | −93.4648 | −105.223 | −83.073 |
| 6 | −89.9842 | −88.2337 | −101.646 | −110.268 | −89.6742 |
| 7 | −94.2468 | −88.2989 | −103.024 | −115.263 | −92.9248 |
| 8 | −97.1084 | −89.2039 | −104.835 | −115.656 | −91.6603 |
| 9 | −101.429 | −90.923 | −107.578 | −118.578 | −94.9918 |
| 10 | −100.18 | −91.4798 | −109.514 | −116.853 | −99.4484 |
| 11 | −97.6016 | −95.8365 | −109.532 | −119.365 | −102.771 |
| 12 | −98.5424 | −93.5117 | −111.764 | −121.777 | −104.292 | b) Covariate significance
The Table below presents a comparison over all treatment groups.

| Analysis Timepoint (N) | Covariate | p_value |
|---|---|---|
| 4 | trt1 | 0.0128 |
| 4 | base | <.0001 |
| 12 | trt1 | 0.0107 |
| 12 | base | <.0001 | c) The Table below presents mean change from baseline by week and treatment:

| Analysis Timepoint (N) | Planned treatment (mg) | LS adjusted mean | Lower 95% confidence limit | Upper 95% confidence limit |
|---|---|---|---|---|
| 4 | 0 | −78.267781 | −93.531339 | −63.004223 |
| 4 | 2.5 | −75.370737 | −91.064629 | −59.676845 |
| 4 | 5 | −66.878234 | −83.400001 | −50.356467 |
| 4 | 10 | −85.563378 | −101.119727 | −70.007030 |
| 4 | 15 | −106.330686 | −122.645517 | −90.015855 |
| 12 | 0 | −104.682568 | −120.535991 | −88.829145 |
| 12 | 2.5 | −89.857250 | −106.157637 | −73.556864 |
| 12 | 5 | −95.915504 | −113.075759 | −78.755249 |
| 12 | 10 | −109.760136 | −125.917663 | −93.602609 |
| 12 | 15 | −130.594733 | −147.540056 | −113.649411 | d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | 2.897044 | −24.495634 | 30.289722 | 0.9970 |
| 4 | 5.0 | 0 | 11.389547 | −16.739876 | 39.518971 | 0.7205 |
| 4 | 10.0 | 0 | −7.295597 | −34.556270 | 19.965075 | 0.9147 |
| 4 | 15.0 | 0 | −28.062905 | −55.994318 | −0.131492 | 0.0485 |
| 12 | 2.5 | 0 | 14.825318 | −13.625957 | 43.276593 | 0.5176 |
| 12 | 5.0 | 0 | 8.767064 | −20.449428 | 37.983557 | 0.8780 |
| 12 | 10.0 | 0 | −5.077568 | −33.391737 | 23.236601 | 0.9785 |
| 12 | 15.0 | 0 | −25.912165 | −54.922995 | 3.098664 | 0.0951 | ii. Relative change (% from baseline) in weekly weighted score
    a) Week-by-week for each group

| Week | 2.5 mg Mean | 5 mg Mean | 10 mg Mean | 15 mg Mean | Placebo Mean |
|---|---|---|---|---|---|
| 0 | 0% | 0% | 0% | 0% | 0% |
| 1 | −22% | −22% | −20% | −19% | −24% |
| 2 | −32% | −32% | −35% | −43% | −40% |
| 3 | −43% | −37% | −47% | −56% | −43% |
| 4 | −47% | −43% | −54% | −66% | −47% |
| 5 | −48% | −46% | −58% | −70% | −51% |
| 6 | −51% | −56% | −64% | −74% | −55% |
| 7 | −53% | −56% | −64% | −78% | −57% |
| 8 | −55% | −56% | −66% | −78% | −57% |
| 9 | −57% | −58% | −67% | −80% | −58% |
| 10 | −57% | −59% | −68% | −79% | −62% |
| 11 | −56% | −61% | −69% | −80% | −64% |
| 12 | −57% | −60% | −70% | −82% | −65% | b) Covariate significance
The Table below presents a comparison over all treatment groups.

| Analysis Timepoint (N) | Covariate | p_value |
|---|---|---|
| 4 | trt1 | 0.0108 |
| 4 | base | 0.4181 |
| 12 | trt1 | 0.0024 |
| 12 | base | 0.0593 | c) The Table below presents mean relative change from baseline by week and treatment

| Analysis Timepoint (N) | Planned treatment (mg) | LS adjusted mean | Lower 95% confidence limit | Upper 95% confidence limit |
|---|---|---|---|---|
| 4 | 0 | −0.474107 | −0.562044 | −0.386170 |
| 4 | 2.5 | −0.473966 | −0.564382 | −0.383549 |
| 4 | 5 | −0.426177 | −0.521362 | −0.330991 |
| 4 | 10 | −0.541886 | −0.631510 | −0.452262 |
| 4 | 15 | −0.650317 | −0.744310 | −0.556323 |
| 12 | 0 | −0.644566 | −0.728624 | −0.560509 |
| 12 | 2.5 | −0.579457 | −0.665884 | −0.493029 |
| 12 | 5 | −0.599251 | −0.690237 | −0.508264 |
| 12 | 10 | −0.699351 | −0.785021 | −0.613681 |
| 12 | 15 | −0.812214 | −0.902061 | −0.722368 | d) The Table below presents differences with placebo by week and treatment

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 2.5 | 0 | −0.473966 | −0.564382 | −0.383549 | 1.0000 |
| 4 | 5.0 | 0 | −0.426177 | −0.521362 | −0.330991 | 0.8833 |
| 4 | 10.0 | 0 | −0.541886 | −0.631510 | −0.452262 | 0.6745 |
| 4 | 15.0 | 0 | −0.650317 | −0.744310 | −0.556323 | 0.0267 |
| 12 | 2.5 | 0 | −0.579457 | −0.665884 | −0.493029 | 0.6744 |
| 12 | 5.0 | 0 | −0.599251 | −0.690237 | −0.508264 | 0.8871 |
| 12 | 10.0 | 0 | −0.699351 | −0.785021 | −0.613681 | 0.7861 |
| 12 | 15.0 | 0 | −0.812214 | −0.902061 | −0.722368 | 0.0276 |

From this Table it can be seen that the 15 mg daily dose generates a statistically significant difference with placebo at 4 weeks (p-value of 0.0267) and at 12 weeks (p-value of 0.0276).

It is particularly striking to observe the low p-values obtained for the 15 mg dose by comparison to the elevated p-values obtained for the 10 mg dose.

B. Vasomotors parameters for the 10 mg and 15 mg groups by comparison to the placebo and inefficient doses (2.5 mg and 5 mg) grouped together Based on the results observed in section A above, it became apparent that the two lowest doses tested (2.5 mg per day and 5 mg per day) did not show efficacy. A further analysis of the results was thus prepared, where data from these two doses were grouped with the placebo dose and compared to the 10 mg and 15 mg doses.

1. Relative change (% from baseline) in weekly frequency of moderate to severe VMS a) Week-by-week for each group

| | 10 mg | | 15 mg | | Placebo with 2.5 and 5 mg | |
|---|---|---|---|---|---|---|
| Week | Mean | SD | Mean | SD | Mean | SD |
| 0 | 0% | 0% | 0% | 0% | 0% | 0% |
| 1 | −21% | 29% | −22% | 33% | −24% | 25% |
| 2 | −37% | 37% | −46% | 34% | −35% | 31% |
| 3 | −48% | 39% | −57% | 34% | −42% | 32% |
| 4 | −55% | 35% | −67% | 30% | −47% | 33% |
| 5 | −60% | 33% | −72% | 28% | −50% | 33% |
| 6 | −65% | 33% | −76% | 26% | −56% | 32% |
| 7 | −66% | 34% | −79% | 25% | −58% | 32% |
| 8 | −68% | 35% | −79% | 26% | −58% | 34% |
| 9 | −69% | 36% | −81% | 24% | −60% | 33% |
| 10 | −70% | 35% | −80% | 27% | −61% | 33% |
| 11 | −70% | 34% | −82% | 25% | −63% | 34% |
| 12 | −72% | 33% | −84% | 23% | −63% | 33% | b) Covariate significance

| Analysis Timepoint (N) | Covariate | p_value |
|---|---|---|
| 4 | trt1 | 0.0039 |
| 4 | base | 0.3935 |
| 4 | SITEPOOL | 0.3308 |
| 12 | trt1 | 0.0017 |
| 12 | base | 0.1244 |
| 12 | SITEPOOL | 0.0957 | c) Pairwise comparisons with placebo (including ineffective doses 2.5 mg and 5 mg)

| Analysis Timepoint (N) | Planned treatment (mg) | LS adjusted mean | Lower 95% confidence limit | Upper 95% confidence limit |
|---|---|---|---|---|
| 4 | 0 | −0.46779276 | −0.521579 | −0.414007 |
| 4 | 10 | −0.54424142 | −0.634204 | −0.454279 |
| 4 | 15 | −0.64752092 | −0.741851 | −0.553191 |
| 12 | 0 | −0.61799510 | −0.669162 | −0.566828 |
| 12 | 10 | −0.70075417 | −0.786337 | −0.615172 |
| 12 | 15 | −0.80058459 | −0.890322 | −0.710847 | d) Differences with placebo (including ineffective doses 2.5 mg and 5 mg)

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 10.0 | 0 | −0.076449 | −0.193421 | 0.040523 | 0.26148 |
| 4 | 15.0 | 0 | −0.179728 | −0.301777 | −0.057679 | 0.00218 |
| 12 | 10.0 | 0 | −0.082759 | −0.194036 | 0.028518 | 0.17979 |
| 12 | 15.0 | 0 | −0.182589 | −0.298696 | −0.066483 | 0.00099 |

As already mentioned under Section A) above it is particularly striking to observe the low p-values obtained for the 15 mg daily dose by comparison to the elevated p-values obtained for the 10 mg daily dose demonstrating the unique relief obtained with the 15 mg daily dose.

2. Relative change (% from baseline) in Hot Flush Weekly Weighted Score:

a) Week-by-week for each group

| | 10 mg | | 15 mg | | Placebo with 2.5 and 5 mg | |
|---|---|---|---|---|---|---|
| Week | Mean | SD | Mean | SD | Mean | SD |
| 0 | 0% | 0% | 0% | 0% | 0% | 0% |
| 1 | −20% | 28% | −22% | 32% | −24% | 25% |
| 2 | −34% | 36% | −45% | 32% | −36% | 30% |
| 3 | −46% | 39% | −56% | 32% | −42% | 31% |
| 4 | −53% | 34% | −66% | 29% | −46% | 32% |
| 5 | −57% | 32% | −70% | 27% | −49% | 33% |
| 6 | −62% | 32% | −72% | 26% | −54% | 32% |
| 7 | −64% | 32% | −75% | 25% | −55% | 31% |
| 8 | −66% | 34% | −76% | 26% | −56% | 32% |
| 9 | −66% | 34% | −78% | 25% | −57% | 31% |
| 10 | −68% | 34% | −77% | 27% | −59% | 32% |
| 11 | −68% | 33% | −79% | 26% | −60% | 33% |
| 12 | −69% | 32% | −81% | 24% | −60% | 32% | b) Covariate significance

| Analysis Timepoint (N) | Covariate | p_value |
|---|---|---|
| 4 | trt1 | 0.0037 |
| 4 | base | 0.5294 |
| 4 | SITEPOOL | 0.3783 |
| 12 | trt1 | 0.0015 |
| 12 | base | 0.0770 |
| 12 | SITEPOOL | 0.0487 | c) Pairwise comparisons with placebo (including ineffective doses 2.5 mg and 5 mg)

| Analysis Timepoint (N) | Planned treatment (mg) | LS adjusted mean | Lower 95% confidence limit | Upper 95% confidence limit |
|---|---|---|---|---|
| 4 | 0 | −0.45362100 | −0.506219 | −0.401023 |
| 4 | 10 | −0.51368261 | −0.601866 | −0.425499 |
| 4 | 15 | −0.63242707 | −0.724866 | −0.539989 |
| 12 | 0 | −0.59132448 | −0.640861 | −0.541788 |
| 12 | 10 | −0.67757463 | −0.760625 | −0.594524 |
| 12 | 15 | −0.76832743 | −0.855386 | −0.681269 | d) Differences with placebo (including ineffective doses 2.5 mg and 5 mg)

| Analysis Timepoint (N) | Higher dose (mg) | Lower dose (mg) | LS adjusted mean | Lower 95% confidence limit | Upper 95% confidence limit | p_value |
|---|---|---|---|---|---|---|
| 4 | 10.0 | 0 | −0.060062 | −0.174760 | 0.054636 | 0.41666 |
| 4 | 15.0 | 0 | −0.178806 | −0.298114 | −0.059498 | 0.00178 |
| 12 | 10.0 | 0 | −0.086250 | −0.194272 | 0.021772 | 0.14044 |
| 12 | 15.0 | 0 | −0.177003 | −0.289367 | −0.064639 | 0.00097 |

As already mentioned under Section A) above, it can be seen that the 15 mg daily dose generates a statistically significant difference with placebo at 4 weeks (p-value of 0.00178) and at 12 weeks (p-value of 0.00097).

Again, it is particularly striking to observe the low p-values obtained for the 15 mg dose by comparison to the elevated p-values obtained for the 10 mg dose.

C. Menopause Rating Scale

The Menopause Rating Scale (MRS) is a health-related quality of life scale allowing the measure of severity of age-/menopause-related complaints by rating a profile of symptoms (Heinemann et al., 2003, "International versions of the Menopause Rating Scale (MRS)" Health Qual Life Outcomes 1: 28; Heinemann et al., 2004, "The Menopause Rating Scale (MRS) scale: A methodological review". Health Qual Life Outcomes 2: 45; Heinemann et al., 2004, "The Menopause Rating Scale (MRS) as outcome measure for hormone treatment? A validation study". Health Qual Life Outcomes 2:67).

The score increases point by point with increasing severity of subjectively perceived complaints in each one of 11 items (severity expressed in 0 to 4 points in each item). By checking these 5 possible boxes of "severity" for each of the items in the questionnaire, the respondent provides her personal perception. The total MRS score ranges between 0 (asymptomatic) to 44 (highest degree of complaints). The minimal/maximal scores vary between three dimensions depending on the number of complaints allocated to the respective dimension of symptoms (Heinemann et al., 2003, *Health Qual Life Outcomes* 1: 28):

1. psychological symptoms: 0 to 16 scoring points (4 symptoms: depressed, irritable, anxious, exhausted);
2. somato-vegetative symptoms: 0 to 16 points (4 symptoms: sweating/flush, cardiac complaints, sleeping disorders, joint & muscle complaints);
3. urogenital symptoms: 0 to 12 points (3 symptoms: sexual problems, urinary complaints, vaginal dryness).

Total MRS Score

|  | 2.5 mg | | 5 mg | | 10 mg | | 15 mg | | Placebo | |
| --- | --- | --- | --- | --- | --- | --- | --- | --- | --- | --- |
| Week | Mean | SD | Mean | SD | Mean | SD | Mean | SD | Mean | SD |
| Baseline | 16.5 | 7.2 | 16.5 | 7.3 | 17.6 | 7.6 | 16.4 | 8.1 | 18.2 | 8.9 |
| Week 4 | 10.3 | 5.6 | 10.5 | 6.7 | 11.7 | 6.8 | 8.7 | 6.2 | 12.8 | 8.0 |
| Week 12 | 9.5 | 6.7 | 11.0 | 7.7 | 9.7 | 6.9 | 8.1 | 5.8 | 11.4 | 7.8 |

The Menopause Rating Scale (MRS) points to an overall improvement in quality of life, with the strongest effect for the 15 mg dose. At this dose, a statistically significant effect was observed by comparison with placebo at week 4, with a p-value of 0.0113 and a near statistically significant effect was observed at week 12, with a p-value of 0.0694.

D. Genito-Urinary Symptoms (GSM)

Change from baseline to week 12 in the following GSM symptoms (VVA subject self-assessment) were recorded:

a) Vaginal dryness (sensation of dryness or burning in the vagina; none=0 mild=1, moderate=2 or severe=3):

| Dose E4 (mg) | Baseline (mean ± SD) | Week 12 (mean ± SD) | p-value vs placebo |
| --- | --- | --- | --- |
| 2.5 | 1 ± 0.90 | 0.5 ± 0.77 | 0.3345 |
| 5 | 1.3 ± 0.94 | 0.7 ± 0.86 | 0.1202 |
| 10 | 1 ± 0.93 | 0.5 ± 0.75 | 0.0798 |
| 15 | 1.1 ± 1.04 | 0.5 ± 0.68 | 0.0291* |
| Placebo | 1.3 ± 1.10 | 0.9 ± 1.02 | |

*p < 0.05 vs placebo at week 12.

b) Vaginal and/or vulvar irritation/itching (sensation of abnormal irritation or sensitive condition in the vagina; none=0, mild=1, moderate=2 or severe=3):

| Dose E4 (mg) | Baseline (mean ± SD) | Week 12 (mean ± SD) | p-value vs placebo |
| --- | --- | --- | --- |
| 2.5 | 0.7 ± 0.96 | 0.3 ± 0.60 | 0.1717 |
| 5 | 0.6 ± 0.90 | 0.4 ± 0.65 | 0.9618 |
| 10 | 0.7 ± 0.87 | 0.3 ± 0.64 | 0.2487 |
| 15 | 0.5 ± 0.85 | 0.4 ± 0.70 | 0.931 |
| Placebo | 0.8 ± 0.92 | 0.5 ± 0.77 | | c) Dysuria (sensation of pain or difficulty in urinating; none=0, mild=1, moderate=2 or severe=3):

| Dose E4 (mg) | Baseline (mean ± SD) | Week 12 (mean ± SD) | p-value vs placebo |
| --- | --- | --- | --- |
| 2.5 | 0.2 ± 0.56 | 0 ± 0.19 | 0.2942 |
| 5 | 0.2 ± 0.56 | 0 ± 0.20 | 0.3488 |
| 10 | 0.2 ± 0.58 | 0.1 ± 0.23 | 0.3386 |
| 15 | 0.3 ± 0.58 | 0.3 ± 0.61 | 0.643 |
| Placebo | 0.2 ± 0.60 | 0.3 ± 0.55 | | d) Vaginal pain associated with sexual activity (sensation of pain with sexual intercourse none=0, mild=1, moderate=2 or severe=3):

| Dose E4 (mg) | Baseline (mean ± SD) | Week 12 (mean ± SD) | p-value vs placebo |
| --- | --- | --- | --- |
| 2.5 | 0.6 ± 0.77 | 0.3 ± 0.73 | 0.0763 |
| 5 | 1 ± 1.07 | 0.5 ± 0.78 | 0.0246* |
| 10 | 0.6 ± 0.77 | 0.2 ± 0.36 | 0.0004** |
| 15 | 0.7 ± 0.90 | 0.3 ± 0.54 | 0.0006** |
| Placebo | 1 ± 1.14 | 0.7 ± 1.01 | |

*p < 0.05 vs placebo at week 12;
**p < 0.001 vs placebo at week 12.

e) Vaginal bleeding associated with sexual activity (loss of blood with sexual intercourse; presence=1 vs. absence=0):

| Dose E4 (mg) | Baseline Presence (%) | Baseline Absence (%) | Week 12 Presence (%) | Week 12 Absence (%) | p-value vs placebo |
| --- | --- | --- | --- | --- | --- |
| 2.5 | 0 | 100 | 0 | 100 | 0.9958 |
| 5 | 6.4 | 91.5# | 0 | 100 | 0.903 |
| 10 | 0 | 100 | 0 | 100 | 0.9955 |
| 15 | 0 | 97.9# | 4.2 | 95.8 | 0.9308 |
| Placebo | 3.6 | 92.7# | 3.6 | 96.4 | |

Some patients had no sexual activity

The evolution of the VVA symptoms points to an overall improvement, with the strongest effect for the 15 mg daily dose. For vaginal pain associated with sexual activity, significant differences with placebo are observed with the doses of 5, 10 and 15 mg daily with p-values of 0.0246, 0.0004 and 0.0006, respectively. Vaginal dryness, however, which is generally considered as the most bothersome symptom, is only significantly improved by the 15 mg daily dose, with a p-value of 0.0291.

E. Measurements Related to Treatment Side Effects

1. Number of patients with biopsies

| Treatment Group | Placebo | 2.5 mg | 5 mg | 10 mg | 15 mg |
| --- | --- | --- | --- | --- | --- |
| Number of patients with biopsies | 4 | 4 | 5 | 11 | 9 |

2. Adverse Events (AEs)

| Treatment Group | Placebo | 2.5 mg | 5 mg | 10 mg | 15 mg |
| --- | --- | --- | --- | --- | --- |
| Count of Treatment Emergent AEs (TEAEs) | 71 | 61 | 63 | 95 | 82 |
| Percentage of patients with severe TEAE | 9.1 | 7.7 | 10.6 | 7.4 | 6.1 |

| Treatment Group | Placebo | 2.5 mg | 5 mg | 10 mg | 15 mg |
|---|---|---|---|---|---|
| Percentage of patients with TEAE leading to Study Discontinuation | 3.6 | 1.9 | 6.4 | 5.6 | 4.1 |

It can be seen from the Table above that the patients in the 15 mg group present less TEAEs than patients in the 10 mg group. In the 10 mg group of patients who had AEs, the average was 3.2 AEs per patient. By comparison, in the 15 mg group, patients who had AEs had on average 2.6 AEs. Globally, those data show that the 15 mg daily dose provides a significant relief of VMS without generating additional AEs for the patients. In addition, there were less requirements for biopsies in the 15 mg per day group than in the 10 mg per day group.

This is confirmed by the following statistical analysis. Using a Poisson regression model with a random effect for the patient and treatment group as a covariate to model the count of TEAEs in the different treatment groups, it can be shown that there is no statistical difference between the treatment groups (p value of 0.099). Second, a chi-square test was used to assess if the prevalence of patients reporting TEAEs in each treatment group was similar. No statistical difference was found between the treatment groups (p value of 0.575).

3. Patients leaving the study

| Treatment Group | Placebo | 2.5 mg | 5 mg | 10 mg | 15 mg |
|---|---|---|---|---|---|
| Number of patients leaving the study | 14 | 9 | 11 | 15 | 8 |

The invention claimed is:

1. A method of alleviating menopause-associated symptoms, comprising orally administering a composition comprising an estetrol component at a daily amount equivalent to about 15 mg of estetrol.

2. The method of claim 1, further comprising administering a progestogenic component.

3. The method of claim 2, wherein said progestogenic component is selected from drospirenone, progesterone and dydrogesterone.

4. The method of claim 2, wherein said progestogenic component is progesterone and is administered at a daily dose of from 50 mg to 200 mg.

5. The method of claim 1, further comprising administering bazedoxifene.

6. The method of claim 2, wherein said progestogenic component is administered in the same composition as the estetrol component.

7. The method of claim 1, wherein the estetrol component is estetrol.

8. The method of claim 1, wherein the composition is formulated as an oral dosage unit.

9. The method of claim 8, wherein the oral dosage unit is formulated as a daily dosage unit.

10. The method of claim 7, wherein the estetrol is estetrol monohydrate.

11. The method of claim 5, wherein said bazedoxifene is administered in the same composition as the estetrol component.

\* \* \* \* \*